(12) United States Patent
Mooberry et al.

(10) Patent No.: US 9,340,572 B2
(45) Date of Patent: May 17, 2016

(54) TACCALONOLIDE MICROTUBULE STABILIZERS

(71) Applicant: THE BOARD OF REGENTS OF THE UNIVERSITY OF TEXAS SYSTEM, Austin, TX (US)

(72) Inventors: Susan L. Mooberry, San Antonio, TX (US); Jiangnan Peng, San Antonio, TX (US); April L. Risinger, San Antonio, TX (US); Jing Li, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/096,876

(22) Filed: Dec. 4, 2013

(65) Prior Publication Data

US 2014/0357608 A1    Dec. 4, 2014

Related U.S. Application Data

(63) Continuation of application No. PCT/US2012/041152, filed on Jun. 6, 2012.

(60) Provisional application No. 61/493,653, filed on Jun. 6, 2011, provisional application No. 61/535,202, filed on Sep. 15, 2011.

(51) Int. Cl.
*C07D 493/08* (2006.01)
*C07J 71/00* (2006.01)

(52) U.S. Cl.
CPC .............. *C07J 71/001* (2013.01); *C07D 493/08* (2013.01); *C07J 71/0005* (2013.01)

(58) Field of Classification Search
CPC .................................................. C07D 493/08
See application file for complete search history.

(56) References Cited

FOREIGN PATENT DOCUMENTS

| WO | WO 00/71563 A2 | 11/2000 |
| WO | WO 01/40256 A1 | 6/2001 |
| WO | WO 2012/170573 A2 | 12/2012 |

OTHER PUBLICATIONS

Muehlbauer, et al. Document No. 140:25475, retrieved from CAPLUS, (2003).*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Bennett et al., *Chem. Biol.*, 17:725-734, 2010.
Boyd and Paull, *Drug Develop. Res.* 34:91-109, 1995.
Chen et al., *Phytochem.*, 27:2999-3002, 1988.
Chen et al., *Planta Medica*, 63:40-43, 1997.
Chen et al., *Tetrahedron Ltrs.*, 28:1673-1676, 1987.
Corbett et al. *Cancer Treat. Rep.*, 62:1471-88,1978.
Fojo and Menefee, *Annual Oncol.*, 18(5):v3-8, 2007.
Galsky et al., *Nat. Rev. Drug Discov.*, 9(9):677-678, 2010.
Huang and Liu, *Helvetica Chimica Acta*, 85:2553-2558, 2002.
Komlodi-Pasztor et al., *Nat Rev Clin Oncol.*, 8:244-250, 2011.
Krishan, *J. Cell Biol.*, 66:188-193, 1975.
Li et al., *J. Am. Chem. Soc.*, 133:19064-19067, 2011.
Morris and Fomier, *Clin. Cancer Res.*, 14(22):7167-7172.
Muhlbauer and Seip, *Helvetica Chimica Acta*, 86:2065-2072, 2003.
Nogales et al., *Nature*, 375:424-427, 1995.
Peng et al., *J Med Chem* Epub Aug. 11, 2011.
Corbett et al., In: *Transplantable Syngeneic Rodent Tumors: Solid Tumors of Mice*, 2nd Ed., Humana Press Inc., Totowa, NJ, 43-78, 2011.
Risinger et al., *Cancer Res.*, 68:8881-8888, 2008.
Shen et al., *Chinese J Chem.*, 9:92-94,1991.
Shen et al., *Phytochem.*, 42:891-893, 1996.
Shen et al., *J. Pharmacal. Exp. Ther.* 337:423-432, 2011.
Skehan et al., *J. Natl. Cancer Inst.*, 82:1107-1112, 1990.
Tinley et al., *Cancer Res.*, 63:3211-3220, 2003.
Yang et al., *Helvetica Chimica Acta*, 91:1077-1082, 2008.
U.S. Appl. No. 61/493,653, filed Jun. 6, 2011.
U.S. Appl. No. 61/535,202, filed Sep. 15, 2011.
International Search Report for the PCT Application, PCT/US2012/041152.

* cited by examiner

*Primary Examiner* — Shawquia Jackson
(74) *Attorney, Agent, or Firm* — Kilpatrick Townsend & Stockton LLP

(57) ABSTRACT

The invention provides epoxytaccalonolide microtubule stabilizers and their use as anti-proliferative microtubule stabilizing agents.

17 Claims, 7 Drawing Sheets

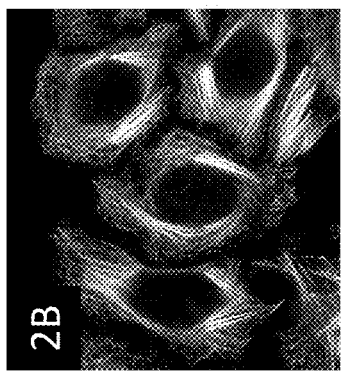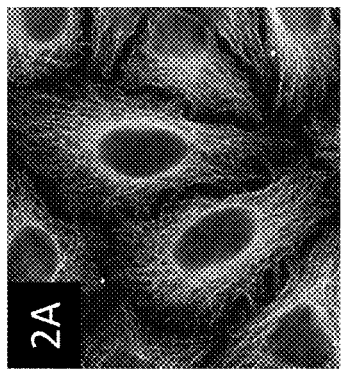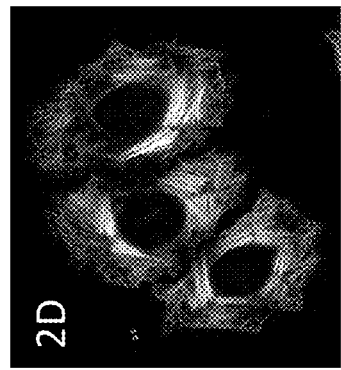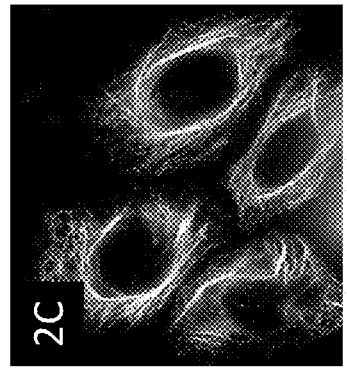
FIGS. 2A-D

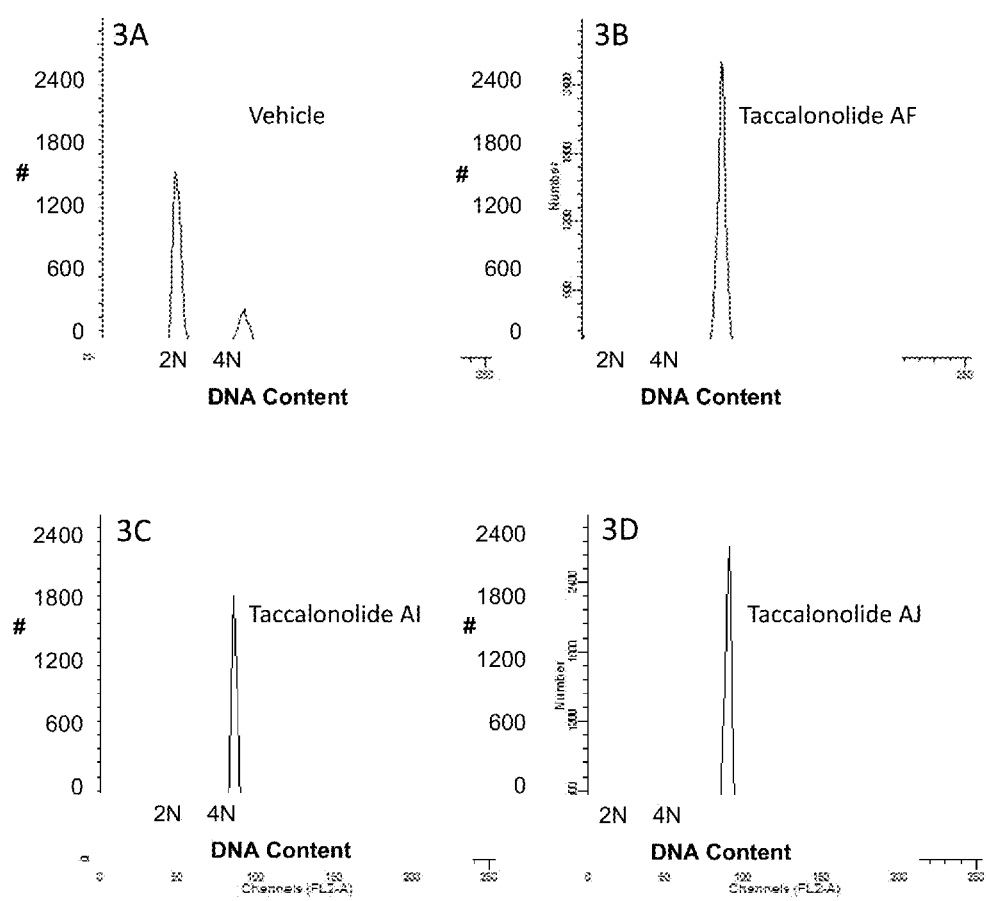
FIGS. 3A-D

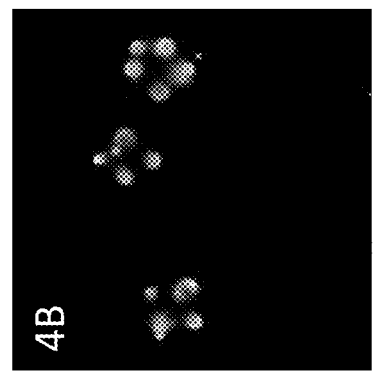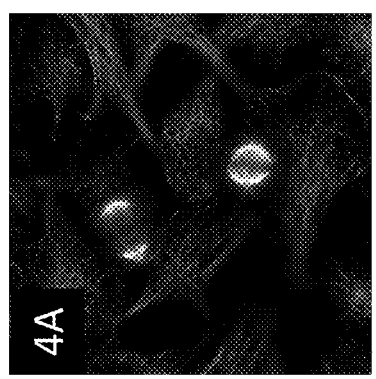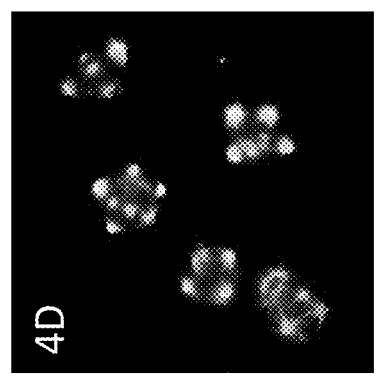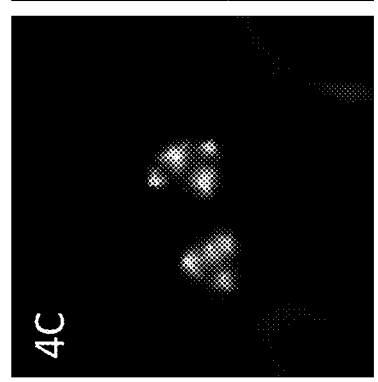
FIGS. 4A-D

|  | AF (nM) | AJ (nM) | Paclitaxel (nM) |
|---|---|---|---|
| HeLa | 23.6 ± 2.1 | 6.6 ± 0.3 | 1.6 ± 0.1 |
| WTβIII | 30.6 ± 3.3 | 11.1 ± 0.6 | 17.8 ± 1.2 |
| (Rr) | (1.3) | (1.7) | (11.3) |
| SK-OV-3 | 79.4 ± 3.5 | 16.3 ± 0.8 | 3.8 ± 0.2 |
| SK-OV-3/MDR-1-6/6 | 366 ± 30.6 | 126 ± 12.8 | 785 ± 88 |
| (Rr) | (4.6) | (7.8) | (207) |
| PC-3 | 128 ± 16 | 25.1 ± 4.0 | 3.7 ± 0.2 |

FIG. 7

TACCALONOLIDE MICROTUBULE STABILIZERS

RELATED APPLICATIONS

This application claims benefit of priority to U.S. Provisional Application Ser. Nos. 61/493,653, filed Jun. 6, 2011, and 61/535,202, filed Sep. 15, 2011, the entire contents of both of which are hereby incorporated by reference.

ACKNOWLEDGEMENT

This invention was made with government support under grant no. CA121138, awarded by the National Institutes of Health. The government has certain rights in the invention.

BACKGROUND OF THE INVENTION

1. Field of the Invention

This invention relates to the fields of medicine and pharmaceuticals. In particular, the invention relates to the identification of taccalonolide microtubule stabilizers for use in inhibiting cell proliferation and disrupting normal cellular microtubule processes leading to cell death.

2. Related Art

Microtubules are cellular structures important for normal cellular metabolism, cellular transport and cell division. Interrupting microtubule dependent processes causes cellular defects including inhibition of proliferation and cellular trafficking leading to initiation of cell death pathways. Microtubule disrupting agents including microtubule stabilizers are one of the most important classes of anticancer therapeutics used in the clinic today. Additionally microtubule stabilizers are used in other human diseases of hyperproliferation including cardiovascular disease, where they are used to coat stents. The taxoid microtubule stabilizer paclitaxel (Taxol™) has been widely used in the treatment of solid tumors, including breast, ovarian and lung cancers for over a decade as a single agent and in combination with targeted therapies. In spite of their clinical utility, the shortcomings of paclitaxel and the second generation semi-synthetic taxoid, docetaxel (Taxotere™), include innate and acquired drug resistance and dose limiting toxicities (Fojo and Menefee, 2007). Two new microtubule stabilizers have been approved for clinical use in the past few years: the epothilone ixabepilone (Ixempra) and the taxoid cabazitaxel (Jevtana), which circumvent some, but not all of the shortcomings of first and second generation microtubule stabilizers (Morris and Fornier, 2008; Galsky et al., 2010, Shen et al., 2011). These microtubule stabilizing drugs all bind to the interior lumen of the intact microtubule at the taxoid binding site, which causes a stabilization of microtubule protofilament interactions and thereby decreases the dynamic nature of microtubules (Nogales et al., 1995).

Two additional classes of microtubule stabilizers have been isolated from nature: laulimalides/peloruside A and the taccalonolides. Laulimalide and peloruside A have recently been shown to bind to the exterior of the microtubule at a site distinct from the taxoid binding site, but result in microtubule stabilization effects nearly identical to the taxoids (Bennett et al., 2010). The microtubule stabilizing properties of the taccalonolides A, E, B and N together with their ability to overcome multiple clinically relevant mechanisms of drug resistance (Risinger et al., 2008) prompted further interest in identifying new taccalonolides.

Intense efforts over the past three decades have identified a large variety of interesting chemical compounds from the roots and rhizomes of *Tacca* species, including 25 taccalonolides, denoted as taccalonolides A-Y (Chen et al., 1987; Chen et al., 1988; Shen et al., 1991; Shen et al., 1996; Chen et al., 1997; WO/2001/040256; Huang and Liu, 2002; Muhlbauer et al., 2003; Yang et al., 2008). However, there have been limited biological studies on the taccalonolides. In 2003, microtubule stabilizing activities of taccalonolides A and E were reported (Tinley et al., 2003). Follow up studies showed preliminary structure-activity relationships (SAR) for the antiproliferative activities of taccalonolides A, E, B and N. The antiproliferative potencies of these four taccalonolides in HeLa cells were all in the mid nanomolar range (190 nM to 644 nM) (Risinger et al., 2008) and further studies showed that the taccalonolides A, E and N have in vivo antitumor activity (Peng et al., 2011). However, a full understanding of the structure activity relationships of the taccalonolides remains to be elucidated. Given that the biological activity profiles of known taccalonolides vary, and in view of the wide variety of diseases that may be treated or prevented with compounds having potent microtubule stabilization effects, and the high degree of unmet medical need represented within this variety of diseases, it is desirable to synthesize new compounds with diverse structures that may have improved biological activity profiles for the treatment of one or more indications.

SUMMARY OF THE INVENTION

Thus, in accordance with the present invention, there are provided novel taccalonolide derivatives with microtubule stabilizing properties, pharmaceutical compositions thereof, methods of their manufacture, and methods for their use, including for the prevention and treatment of mammalian cell hyperproliferation and initiation of cell death.

In one aspect of the invention, there are provided compounds of the formula:

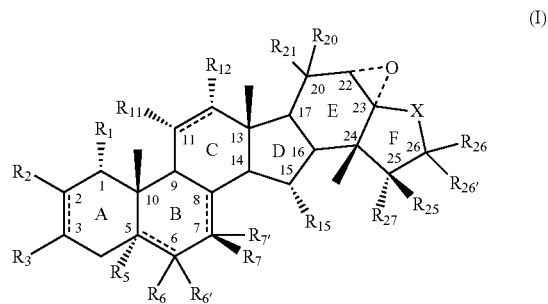

wherein:

$R_1$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_2$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof, or $R_2$ is taken together with $R_3$ to form an epoxide at C-2/C-3;

$R_3$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, and substituted versions thereof, or $R_3$ is taken together with $R_2$ as defined above;

R$_5$ is absent, hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_6$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if R$_e$ is not present, or R$_6$ is taken together with R$_7$ to form an epoxide at C-6/C-7;

R$_{6'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_7$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if R$_7$ is not present, or R$_7$ is taken together with R$_6$ as defined above;

R$_{11'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{11}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{12}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{15}$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{20}$ is hydrogen, amino, cyano, azido, halo, hydroxy, hydroperoxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{21}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{25}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{26}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if R$_{26'}$ is not present;

R$_{26'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

R$_{27}$ is hydrogen, amino, cyano, azido, halo, hydroxy, alkyl$_{(C\leq12)}$; alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof; and X is O, NR' or CR'$_2$, wherein each R' is independently hydrogen or alkyl$_{(C\leq6)}$;

or a pharmaceutically acceptable salt thereof.

In some embodiments,

R$_1$ is hydroxy, alkoxy$_{(C\leq12)}$ or acyloxy$_{(C\leq12)}$;

R$_2$ is hydroxy, halogen, or R$_2$ is taken together with R$_3$ to form an epoxide at C-2/C-3;

R$_3$ is hydroxy, halo, or R$_2$ is taken together with R$_3$ as defined above;

R$_5$ is hydrogen, hydroxy, amino, alkoxy$_{(C\leq9)}$, alkylamino$_{(C\leq6)}$, or dialkylamino$_{(C\leq12)}$;

R$_6$ is hydrogen, hydroxy, alkoxy$_{(C\leq8)}$, acyloxy$_{(C\leq8)}$, or oxo;

R$_{6'}$ when present is hydrogen or hydroxy, alkoxy$_{(C\leq8)}$ or acyloxy$_{(C\leq8)}$;

R$_7$ is hydrogen, hydroxy, alkoxy$_{(C\leq8)}$, acyloxy$_{(C\leq8)}$, or oxo if R$_{7'}$ is not present;

R$_{7'}$ when present is hydrogen, hydroxy, alkoxy$_{(C\leq8)}$, or acyloxy$_{(C\leq8)}$;

R$_{11}$ is hydrogen, hydroxy, alkyl$_{(C\leq6)}$, alkoxy$_{(C\leq8)}$, or acyloxy$_{(C\leq8)}$;

R$_{12}$ is hydrogen, hydroxy, alkyl$_{(C\leq6)}$, alkoxy$_{(C\leq8)}$, or acyloxy$_{(C\leq8)}$;

R$_{15}$ is hydrogen, hydroxy, alkyl$_{(C\leq6)}$, alkoxy$_{(C\leq8)}$ or acyloxy$_{(C\leq8)}$;

R$_{20}$ is hydrogen, hydroxy, hydroperoxy, alkoxy$_{(C\leq8)}$ or acyloxy$_{(C\leq8)}$;

R$_{21}$ is hydrogen or alkyl$_{(C\leq6)}$;

R$_{25}$ is hydrogen, hydroxy, alkoxy$_{(C\leq8)}$ or acyloxy$_{(C\leq8)}$;

R$_{26}$ is hydrogen, hydroxy, alkoxy$_{(C\leq8)}$ or oxo if R$_{26'}$ is not present;

R$_{26'}$ when present is hydrogen, hydroxy or alkoxy$_{(C\leq8)}$;

R$_{27}$ is hydrogen or alkyl$_{(C\leq6)}$; and

X is O, NR' or CR'$_2$, wherein each R' is independently hydrogen or alkyl$_{(C\leq6)}$;

or a pharmaceutically acceptable salt thereof

In some embodiments, R$_1$ is acyloxy$_{(C\leq12)}$. In some embodiments, R$_1$ is acetyloxy. In some embodiments, R$_1$ is acyloxy$_{(C3-12)}$. In some embodiments, R$_1$ is hydroxy. In some embodiments, R$_2$ is acyloxy$_{(C\leq12)}$. In some embodiments, R$_2$ is acetyloxy. In some embodiments, R$_2$ and R$_3$ are taken together to form an epoxide at C-2/C-3. In some embodiments, R$_3$ is chloro. In some embodiments, R$_5$ is hydrogen. In some embodiments, R$_5$ is hydroxy. In some embodiments, R$_5$ is absent. In some embodiments, R$_6$ is oxo. In some embodiments, R$_6$ is hydroxy. In some embodiments, R$_6$ is acyloxy$_{(C\leq12)}$. In some embodiments, R$_6$ is acetyloxy. In some embodiments, R$_6$ and R$_7$ are taken together to form an epoxide at C-6/C-7. In some embodiments, R$_e$ is absent. In some embodiments, R$_e$ is hydrogen. In some embodiments, R$_7$ is acyloxy$_{(C\leq12)}$. In some embodiments, R$_7$ is acetyloxy. In some embodiments, R$_7$ is hydroxy. In some embodiments, R$_7$ is oxo. In some embodiments, R$_{7'}$ is hydrogen. In some embodiments, R$_{7'}$ is hydroxy. In some embodiments, R$_{11}$ is acyloxy$_{(C\leq12)}$. In some embodiments, R$_{11}$ is acetyloxy. In some embodiments, R$_{11}$ is hydrogen. In some embodiments, R$_{11}$ is substituted acyloxy$_{(C\leq12)}$. In some embodiments, R$_{11}$ is hydroxy. In some embodiments, R$_{12}$ is acyloxy$_{(C\leq12)}$. In some embodiments, R$_{12}$ is acetyloxy. In some embodiments, R$_{12}$ is hydroxy. In some embodiments, R$_{15}$ is hydroxy. In some embodiments, R$_{15}$ is hydrogen. In some embodiments, R$_{15}$ is oxo. In some embodiments, R$_{15}$ is acyloxy$_{(C\leq12)}$. In some embodiments, R$_{15}$ is acetyloxy. In some embodiments, R$_{20}$ is methyl. In some embodiments, R$_{20}$ is hydroxy. In some embodiments, R$_{20}$ is hydroperoxy. In some embodiments, R$_{21}$ is hydrogen. In some embodiments, X is O. In some embodiments, R$_{25}$ is hydroxy. In some embodiments, R$_{25}$ is acetyloxy. In some embodiments, R$_{26}$ is oxo. In some embodiments, R$_{26'}$ is absent. In some embodiments, R$_{27}$ is methyl. In some embodiments, C7/C8 are connected with a double bond. In some embodiments, R$_5$ is a hydroxy or alkyl$_{(C\leq6)}$.

In some embodiments, the compounds are further defined as:

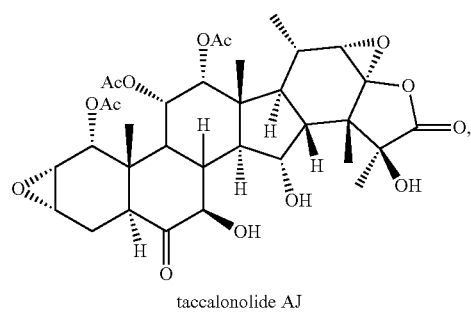

taccalonolide AJ

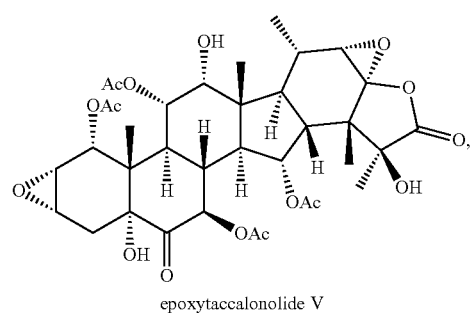

epoxytaccalonolide V

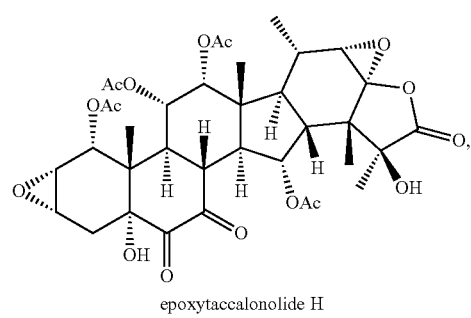

epoxytaccalonolide H

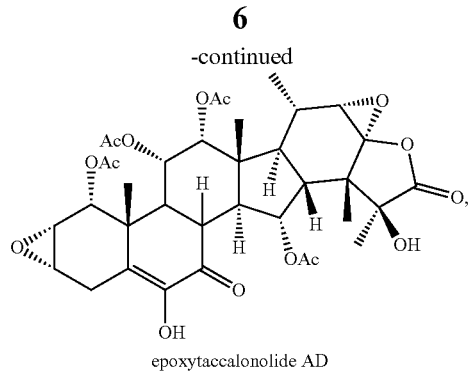

epoxytaccalonolide AD

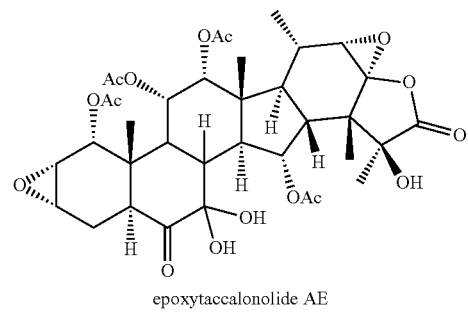

epoxytaccalonolide AE

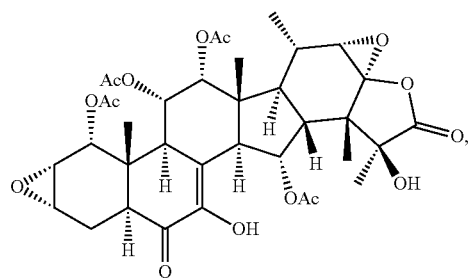

epoxytaccalonolide H2

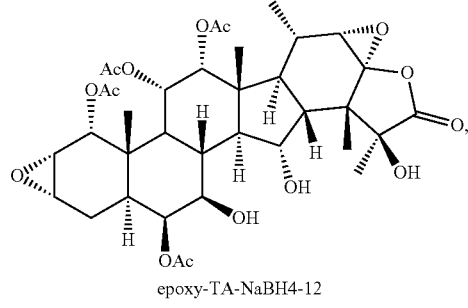

epoxy-TA-NaBH4-12

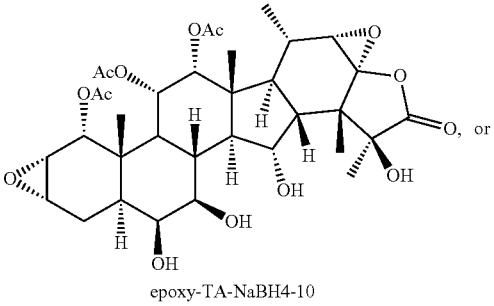

epoxy-TA-NaBH4-10

-continued

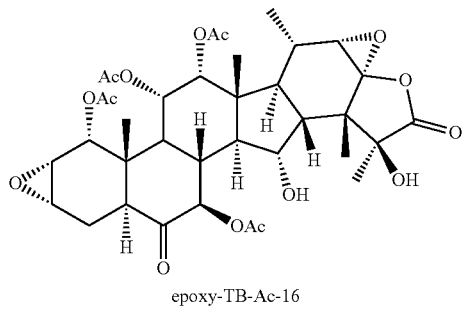

epoxy-TB-Ac-16

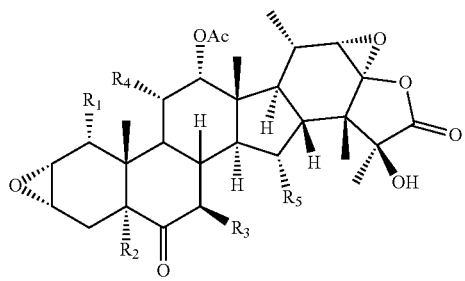

taccalonolide AF: $R_1$ = OAc $R_2$ = H $R_3$ = OH $R_4$ = $R_5$ = OAc
epoxytaccalonolide D: $R_1$ = OAc $R_2$ = H $R_3$ = OAc $R_4$ = OAc $R_5$ = OH
epoxytaccalonolide E: $R_1$ = OAc $R_2$ = H $R_3$ = OH $R_4$ = H $R_5$ = OAc
epoxytaccalonolide F: $R_1$ = OAc $R_2$ = H $R_3$ = OH $R_4$ = OH $R_5$ = OAc
epoxytaccalonolide L: $R_1$ = OAc $R_2$ = H $R_3$ = OH $R_4$ = OC(O)CH$_2$OH $R_5$ = OAc
epoxytaccalonolide N: $R_1$ = OAc $R_2$ = H $R_3$ = OH $R_4$ = H $R_5$ = OH
epoxytaccalonolide G: $R_1$ = OAc $R_2$ = OH $R_3$ = OH $R_4$ = H $R_5$ = H
epoxytaccalonolide R: $R_1$ = OAc $R_2$ = H $R_3$ = OAc $R_4$ = H $R_5$ = OAc epoxytaccalonolide S: $R_1$ = isobutyrate $R_2$ = H $R_3$ = OH $R_4$ = H $R_5$ = OAc
epoxytaccalonolide T: $R_1$ = 3-methylbutanoate $R_2$ = OH $R_3$ = OAc $R_4$ = H $R_5$ = OAc
epoxytaccalonolide U: $R_1$ = OH $R_2$ = OH $R_3$ = OAc $R_4$ = H $R_5$ = OAc
epoxytaccalonolide Z: $R_1$ = OAc $R_2$ = OH $R_3$ = OH $R_4$ = $R_5$ = OAc
epoxytaccalonolide AA: $R_1$ = OAc $R_2$ = OH $R_3$ = $R_4$ = $R_5$ = OAc
epoxytaccalonolide AB: $R_1$ = OAc $R_2$ = OH $R_3$ = OH $R_4$ = OAc $R_5$ = OH
epoxytaccalonolide AG: $R_1$ = 3-methylbutanoate $R_2$ = OH $R_3$ = OH $R_4$ = H $R_5$ = OAc
epoxytaccalonolide AH: $R_1$ = 3-methylbutanoate $R_2$ = H $R_3$ = OH $R_4$ = H $R_5$ = OAc
epoxytaccalonolide AI: $R_1$ = 3-methylbutanoate $R_2$ = H $R_3$ = OH $R_4$ = H $R_5$ = OH

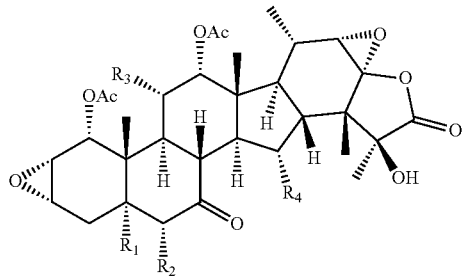

epoxytaccalonolide I: $R_1$ = H $R_2$ = OH $R_3$ = OAc $R_4$ = OH
epoxytaccalonolide J: $R_1$ = H $R_2$ = OH $R_3$ = OAc $R_4$ = OAc
epoxytaccalonolide K: $R_1$ = OH $R_2$ = OH $R_3$ = OAc $R_4$ = OH
epoxytaccalonolide M: $R_1$ = OH $R_2$ = OH $R_3$ = H $R_4$ = oxo -continued

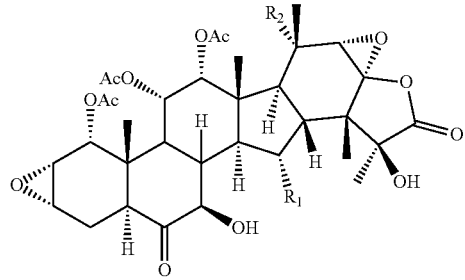

epoxytaccalonolide W: $R_1$ = OH $R_2$ = OH
epoxytaccalonolide AC: $R_1$ = OAc $R_2$ = OOH or a pharmaceutically acceptable salt thereof In another aspect there are provided compounds selected from the group consisting of:

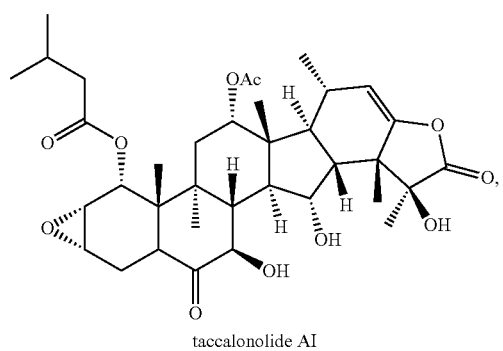

taccalonolide AI

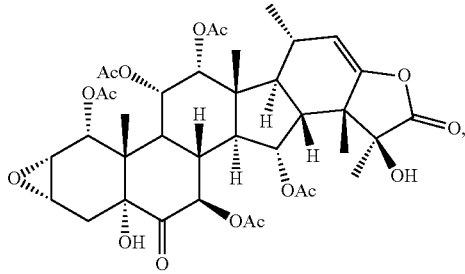

taccalonolide AA

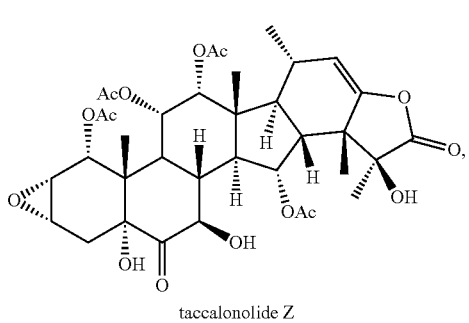

taccalonolide Z

-continued
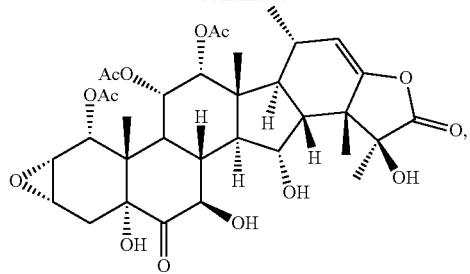
taccalonolide AB
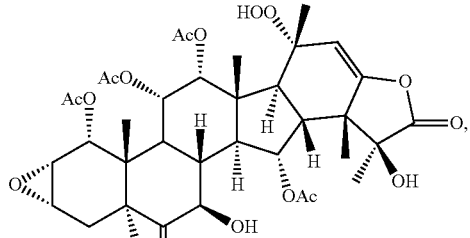
taccalonolide AC
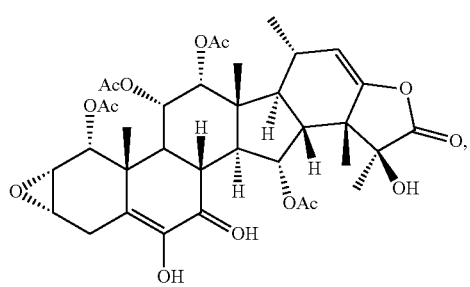
taccalonolide AD
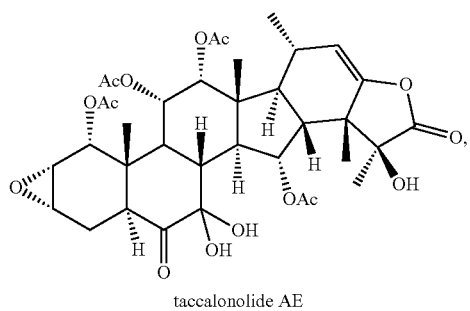
taccalonolide AE
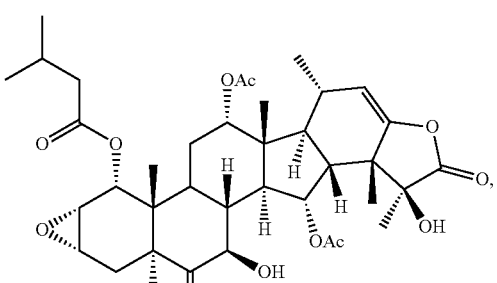
taccalonolide AG
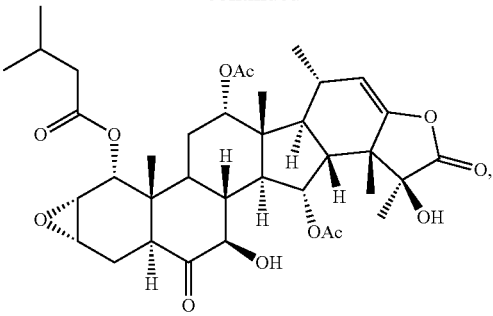
taccalonolide AH
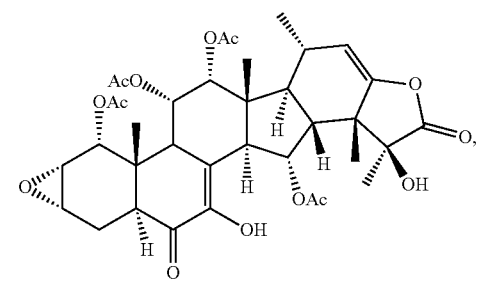
taccalonolide H2
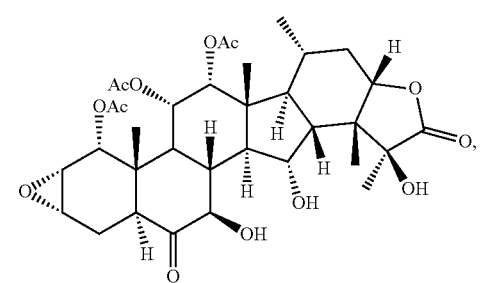
dihydrotaccalonolide B
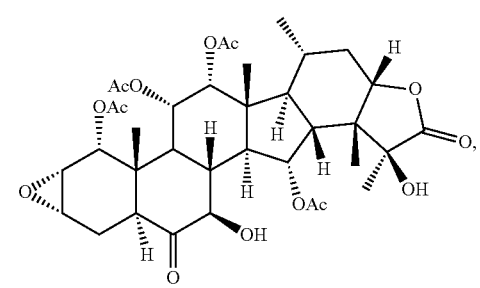
dihydrotaccalonolide A
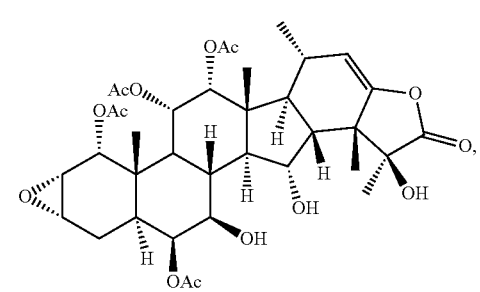
TA-NaBH4-12

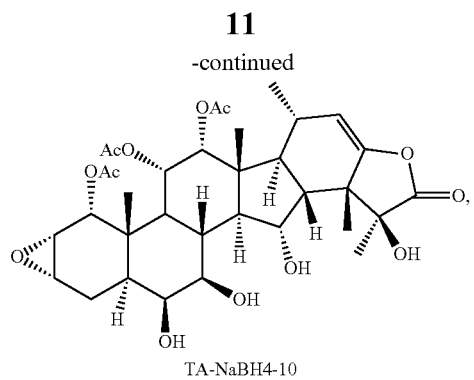
TA-NaBH4-10
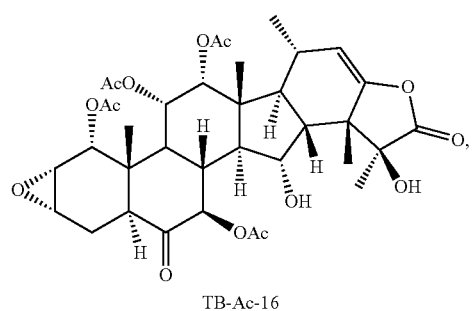
TB-Ac-16
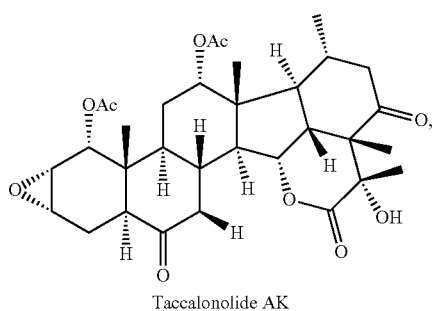
Taccalonolide AK
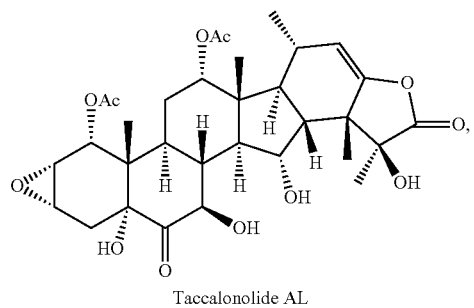
Taccalonolide AL
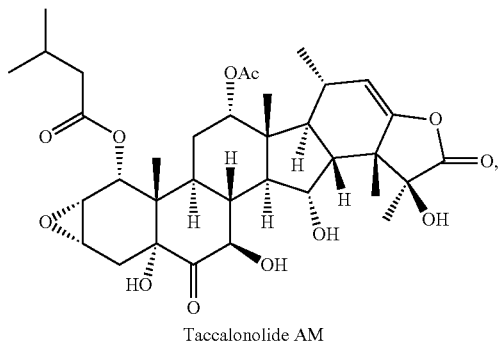
Taccalonolide AM
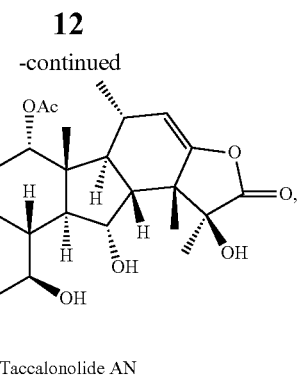
Taccalonolide AN
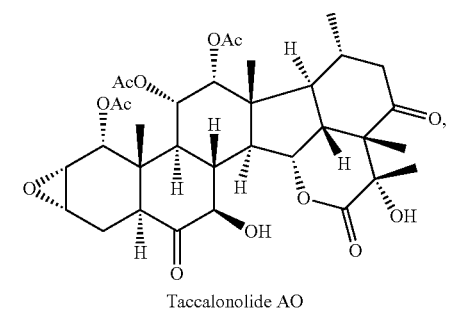
Taccalonolide AO
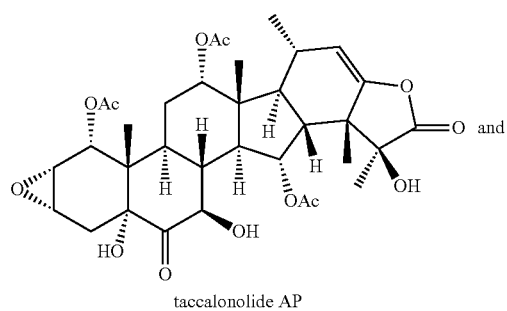
taccalonolide AP
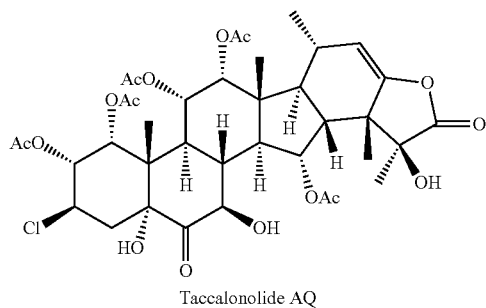
Taccalonolide AQ
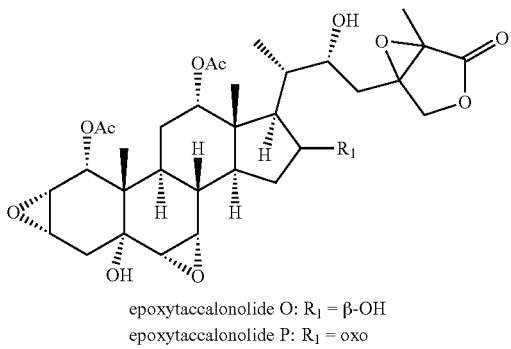
epoxytaccalonolide O: $R_1$ = β-OH
epoxytaccalonolide P: $R_1$ = oxo

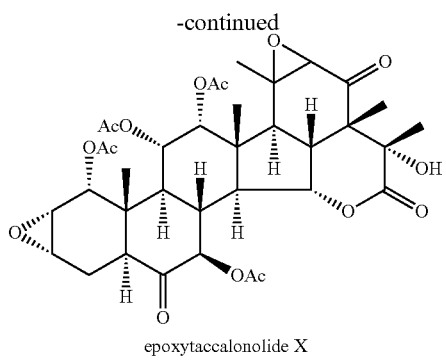

epoxytaccalonolide X or a pharmaceutically acceptable salt thereof.

In some embodiments, the compound is at least 90% pure by weight. In some embodiments, the compound is at least 95% pure by weight. In some embodiments, the compound was isolated from plant cell tissue. In some embodiments, the compound was not isolated from cell tissue.

In another aspect there are provided pharmaceutical compositions comprising a compound disclosed herein and a pharmaceutically acceptable carrier. In some embodiments, the composition is formulated for oral administration. In some embodiments, the compositions further comprise one or more pharmaceutically acceptable excipients. In some embodiments, the composition is formulated for controlled release.

In another aspect there are provided methods of treating a hyperproliferative disorder in a patient, the method comprising administering to a patient in need thereof an effective amount of a compound disclosed herein. In some embodiments, the hyperproliferative disorder is cancer. In some embodiments, the cancer is lung cancer, brain cancer, head & neck cancer, breast cancer, skin cancer, liver cancer, pancreatic cancer, prostate cancer, stomach cancer, colon cancer, rectal cancer, uterine cancer, cervical cancer, ovarian cancer, testicular cancer, skin cancer, oral cancer or esophageal cancer. In some embodiments, the hyperproliferative disorder is leukemia, lymphoma or myeloma. In some embodiments, the hyperproliferative disorder is acute myeloid leukemia, chronic myelogenous leukemia or multiple myeloma. In some embodiments, the patient is human.

In another aspect there are provided methods of producing a mixture of epoxytaccalonolides comprising: (a) dissolving a taccalonide-containing a crude extract of the roots and/or rhizomes of a *Tacca* species in an organic solvent; and (b) subjecting the solution of (a) to epoxidation. In some embodiments, the *Tacca* species is *T. chantrieri, T. integrifolia, T. plantaginea, T. pinnatifida leontopetaloides* or *T. cristata aspera*. In some embodiments, the organic solvent is $CH_2Cl_2$, $CH_3Cl$, ethylacetate, dimethyl ether, acetone, methanol, ethanol or isopropanol. In some embodiments, the solution of step (a) is maintained at about −70 to about 40° C. In some embodiments, tep (b) comprises contacting the solution of step (a) with dimethyldioxirane, peracide or hydroperoxide at about −70 to about 70° C. until complete. In some embodiments, wherein step (b) comprises contacting the solution of step (a) with about 1 to about 10 equivalents of 0.01-0.2M dimethyldioxirane. In some embodiments, further comprising evaporating the solvents and reagents of step (b) to isolate said epoxytaccalonolides.

In some embodiments, the structure of taccalonolides and epoxytaccalonolides are illustrated by:

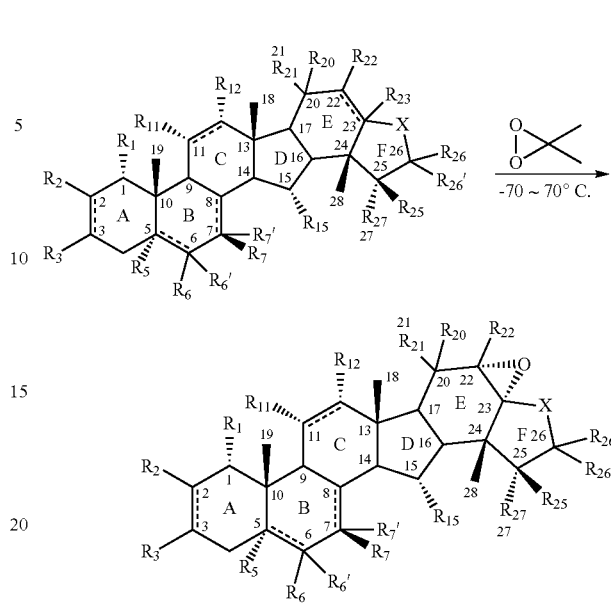

wherein:
$R_1$ is hydrogen, amino, cyano, azido, halo, hydroxy, oxo, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof;

$R_2$ is hydrogen, amino, cyano, azido, halo, hydroxy, oxo, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof, or $R_2$ is taken together with $R_3$ to form an epoxide at C-2/C-3;

$R_3$ is hydrogen, amino, cyano, azido, halo, hydroxy, oxo, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, and substituted versions thereof, or $R_3$ is taken together with $R_2$ as defined above;

$R_5$ is absent, hydrogen, amino, cyano, azido, halo, hydroxy, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof;

$R_6$ is hydrogen, amino, cyano, azido, halo, hydroxy, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof, or oxo if $R_6$ is not present, or $R_6$ is taken together with $R_7$ to form an epoxide at C-6/C-7;

$R_{6'}$ when present is hydrogen, amino, cyano, azido, halo, hydroxy, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof;

$R_7$ is hydrogen, amino, cyano, azido, halo, hydroxy, alkyl$_{(C\le12)}$, alkenyl$_{(C\le12)}$, alkoxy$_{(C\le12)}$, acyl$_{(C\le12)}$, acyloxy$_{(C\le12)}$, alkylamino$_{(C\le12)}$, dialkylamino$_{(C\le12)}$, amido$_{(C\le12)}$, alkylthio$_{(C\le12)}$, aryl$_{(C\le12)}$, aralkyl$_{(C\le12)}$, heterocycloalkyl$_{(C\le12)}$, or substituted versions thereof, or oxo if $R_7$ is not present, or $R_7$ is taken together with $R_6$ as defined above;

$R_7$, when present is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{11}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{12}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{15}$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{20}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{21}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{25}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{26}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof, or oxo if $R_{26'}$ is not present;

$R_{26'}$ when present is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_{27}$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof; and X is O, NR' or CR'$_2$, wherein each R' is independently hydrogen or alkyl$_{(C \leq 6)}$.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 2A-D—Effect of the taccalonolides on interphase cells. HeLa cells were treated for 18 h with vehicle (FIG. 2A), 200 nM taccalonolide AF (FIG. 2B), 200 nM taccalonolide AI (FIG. 2C), or 70 nM taccalonolide AJ (FIG. 2D). Interphase microtubule structures were visualized by indirect immunofluorescence using a β-tubulin antibody.

FIGS. 3A-D—Effect of the taccalonolides on cell cycle distribution. HeLa cells were treated with vehicle (FIG. 3A), 125 nM taccalonolide AF (FIG. 3B), 200 nM taccalonolide AI (FIG. 3C), or 35 nM taccalonolide AJ (FIG. 3D) for 18 h and stained with Krishan's reagent. Cell cycle profile was analyzed by flow cytometry.

FIGS. 4A-D—Effect of the taccalonolides on mitotic spindles. HeLa cells were treated for 18 h with vehicle (FIG. 4A), 125 nM taccalonolide AF (FIG. 4B), 200 nM taccalonolide AI (FIG. 4C), or 35 nM taccalonolide AJ (FIG. 4D). The microtubule structures in mitotic cells were visualized by indirect immunofluorescence using a β-tubulin antibody.

FIG. 7—Effect of the taccalonolides in drug resistant and sensitive cells. IC$_{50}$ values for inhibition of cellular proliferation for taccalonolides AF and AJ were determined in drug sensitive and drug resistant cell lines. The HeLa cell pair evaluated the effect of βIII tubulin expression on cell sensitivity and the ability of compounds to overcome drug resistance mediated by βIII tubulin expression. The SK-OV-3 cell line pair was used to evaluate the effects of the expression of P-glycoprotein (Pgp) on cell sensitivity and the ability of compounds to overcome Pgp-mediated drug resistence. The effects of the taccalonolides on the drug senstive prostate cancer cell line PC-3 are also presented. IC$_{50}$ values were calculated from an average of 3-4 independent experiments, each performed in triplicate.

DESCRIPTION OF ILLUSTRATIVE EMBODIMENTS

Figure 1:
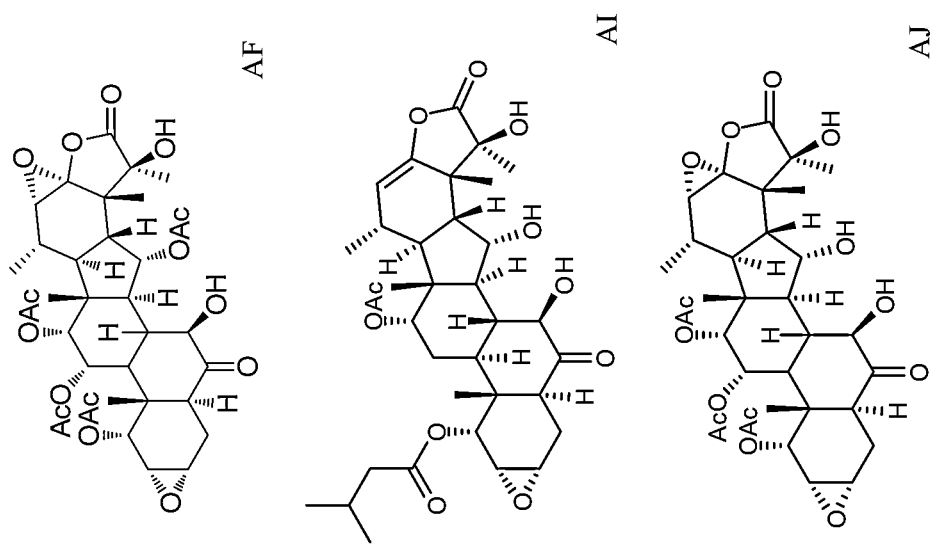
FIG. 1—Structures of the taccalonolides AF, AJ, and AI.

The taccalonolides are a unique class of microtubule stabilizers with activity against drug resistant cells in vitro and in vivo. In the work described below, the inventors generated by isolation and semi-synthesis new taccalonolides including taccalonolides AF, AJ and AI-epo.

Taccalonolide structures were determined by 1D and 2D NMR methods. Each of these taccalonolides stabilizes cellular microtubules, causing the formation of microtubule bundles and mitotic accumulation of cancer cells with multiple abnormal mitotic spindles. $IC_{50}$ values range from the low nanomolar range for taccalonolide AI-epo (0.73 nM) and taccalonolide AJ (4.3 nM) to the low micromolar range for taccalonolide R (13 µM). These studies demonstrate that diverse taccalonolides possess microtubule stabilizing properties and that significant structure-activity relationships exist. These and other aspects of the invention are discussed further below.

I. TACCALONOLIDES

A. Background

The taccalonolides are a class of structurally and mechanistically distinct microtubule-stabilizing agents isolated from *Tacca chantrieri*. An important feature of the taxane family of microtubule stabilizers is their susceptibility to cellular resistance mechanisms including overexpression of P-glycoprotein (Pgp), multidrug resistance protein 7 (MRP7), and the βIII isotype of tubulin. The inventors have previously studied the ability of four taccalonolides, A, E, B, and N, to circumvent these multidrug resistance mechanisms.

Taccalonolides A, E, B, and N were found to be effective in vitro against cell lines that overexpress Pgp and MRP7 (Risinger et al., 2008). In addition, taccalonolides A and E were highly active in vivo against a doxorubicin- and paclitaxel-resistant Pgp-expressing tumor, Mam17/ADR (Risinger et al., 2008). An isogenic HeLa-derived cell line that expresses the βIII isotype of tubulin was used to evaluate the effect of βIII-tubulin on drug sensitivity. When compared with parental HeLa cells, the βIII-tubulin-overexpressing cell line was less sensitive to paclitaxel, docetaxel, epothilone B, and vinblastine (Risinger et al., 2008). In contrast, the βIII-tubulin-overexpressing cell line showed greater sensitivity to all four taccalonolides (Risinger et al., 2008). These data suggest that the taccalonolides have advantages over the taxanes in their ability to circumvent multiple drug resistance mechanisms. The ability of the taccalonolides to overcome clinically relevant mechanisms of drug resistance in vitro and in vivo confirmed that the taccalonolides represent a valuable addition to the family of microtubule-stabilizing compounds with clinical potential (Risinger et al., 2008).

Taccalonolides have also been identified in *Tacca plantaginea*, *Tacca integrifolia*, *Tacca subflaellata* and *Tacca paxiana*.

B. New Taccalonolides

The compounds provided by the present disclosure are shown above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutical research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form, Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable, Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC$(CH_3)_3$), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Examples of compounds provided by the present invention include:

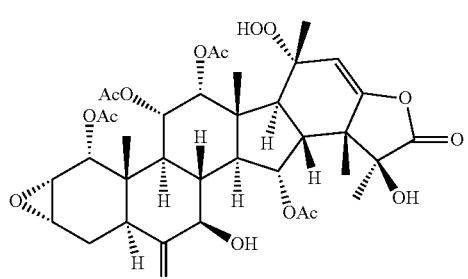

taccalonolide AC

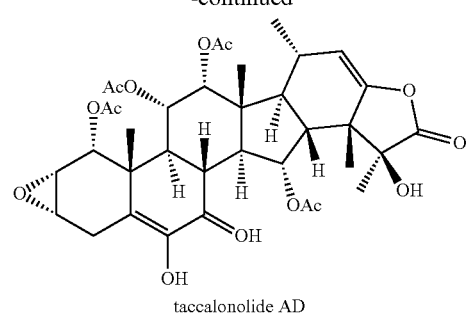

taccalonolide AD

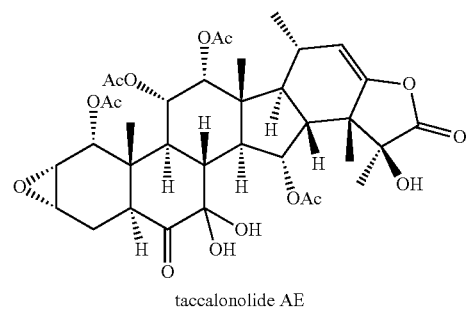

taccalonolide AE

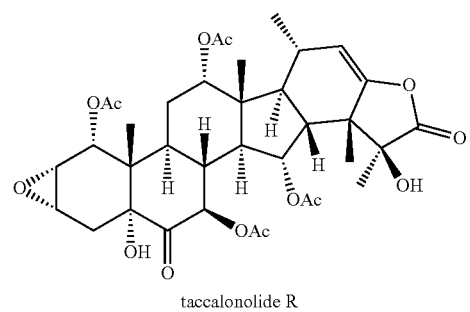

taccalonolide R

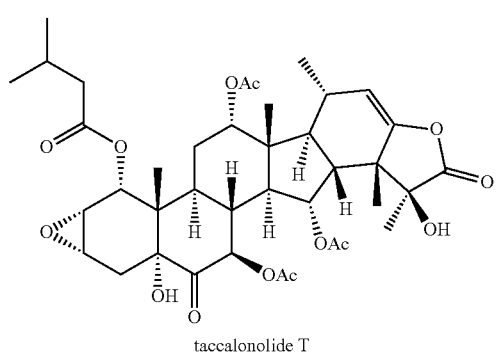

taccalonolide T

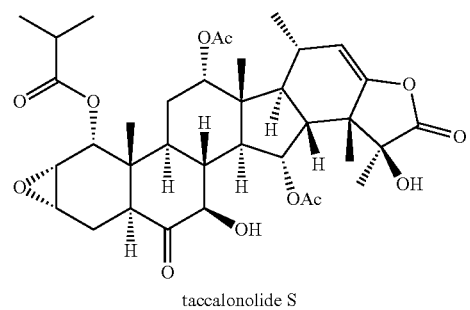

taccalonolide S

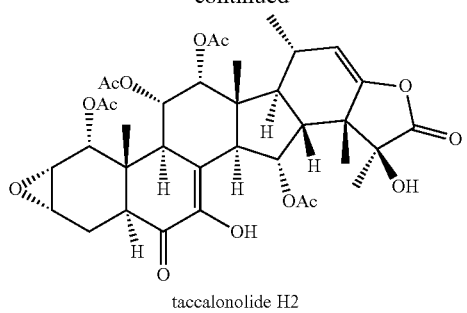
taccalonolide H2

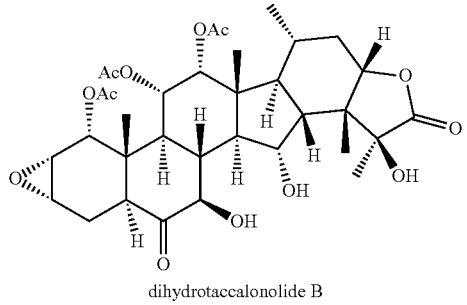
dihydrotaccalonolide B

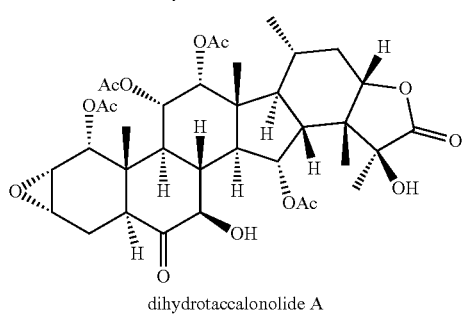
dihydrotaccalonolide A

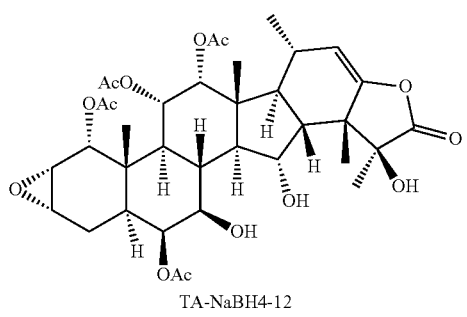
TA-NaBH4-12

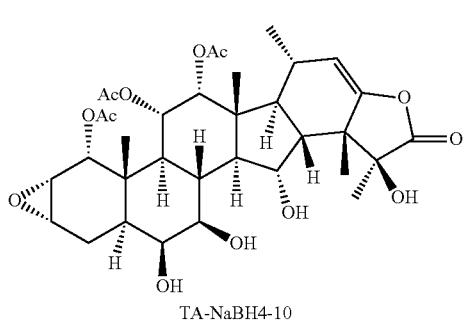
TA-NaBH4-10

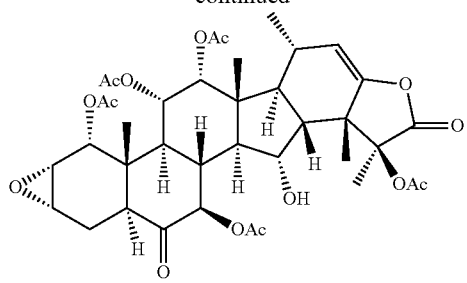
TB-Ac-16

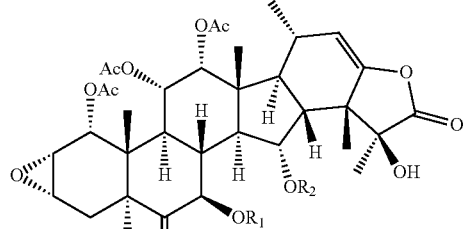

taccalonolide Z: R$_1$ = H    R$_2$ = Ac
taccalonolide AA: R$_1$ = Ac   R$_2$ = Ac
taccalonolide AB: R$_1$ = H    R$_2$ = H

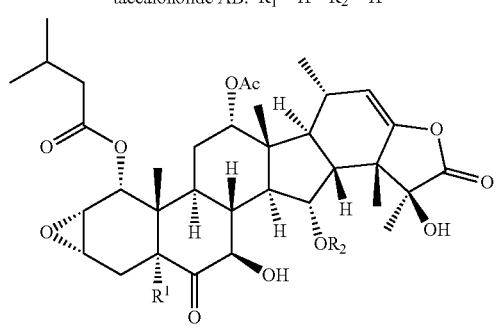

taccalonolide AG: R$_1$ = OH  R$_2$ = Ac
taccalonolide AH: R$_1$ = H   R$_2$ = Ac
taccalonolide AI: R$_1$ = H   R$_2$ = H
taccalonolide AM: R$_1$ = OH  R$_2$ = H

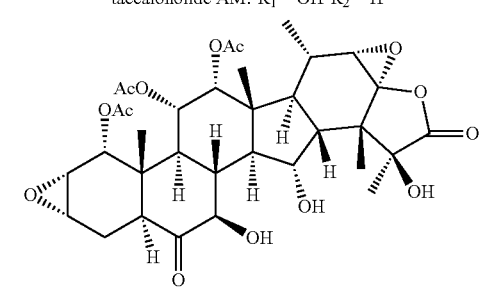
taccalonolide AJ

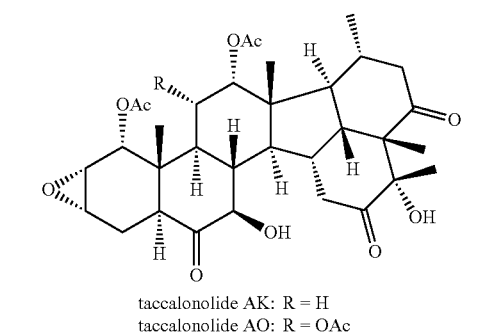
taccalonolide AK: R = H
taccalonolide AO: R = OAc

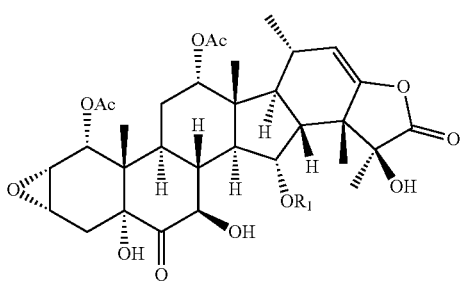

taccalonolide AL: $R_1 = H$
taccalonolide AP: $R_1 = Ac$

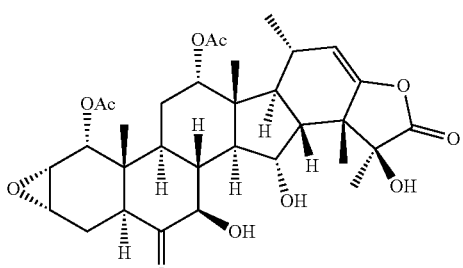

Taccalonolide AN

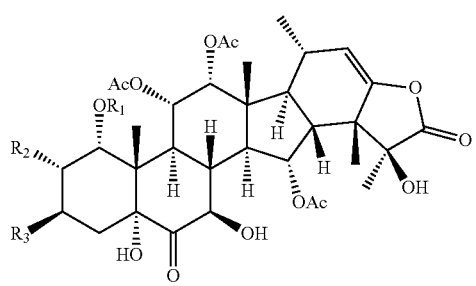

taccalonolide AQ: $R_1 = H$ $R_2 = AcO$ $R_3 = Cl$
taccalonolide AS: $R_1 = Ac$ $R_2 = OH$ $R_3 = Cl$

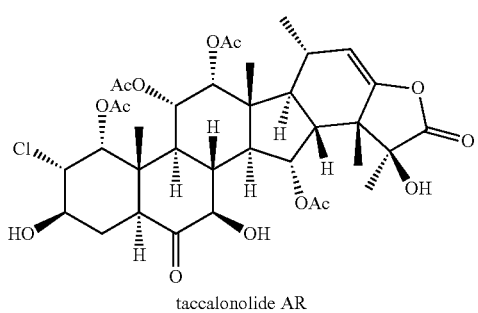

taccalonolide AR

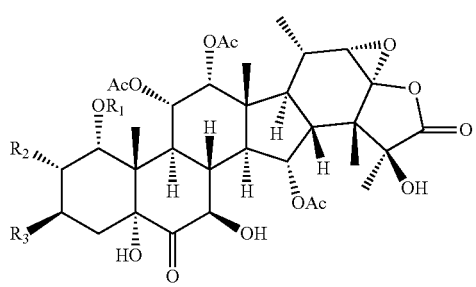

epoxytaccalonolide AQ: $R_1 = H$ $R_2 = AcO$ $R_3 = Cl$
epoxytaccalonolide AS: $R_1 = Ac$ $R_2 = OH$ $R_3 = Cl$

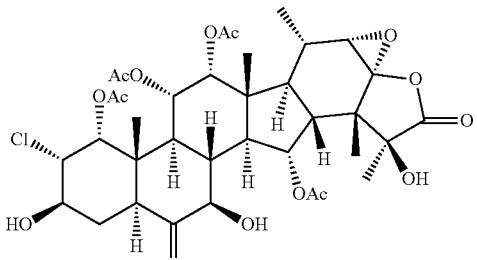

epoxytaccalonolide AR

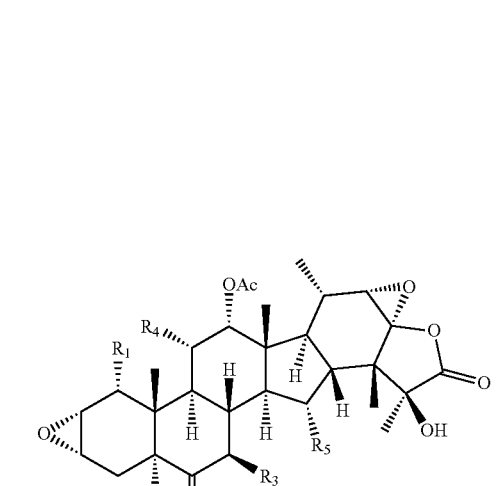

taccalonolide AF: $R_1 = OAc$ $R_2 = H$ $R_3 = OH$ $R_4 = R_5 = OAc$
epoxytaccalonolide D: $R_1 = OAc$ $R_2 = H$ $R_3 = OAc$ $R_4 = OAc$ $R_5 = OH$
epoxytaccalonolide E: $R_1 = OAc$ $R_2 = H$ $R_3 = OH$ $R_4 = H$ $R_5 = OAc$
epoxytaccalonolide F: $R_1 = OAc$ $R_2 = H$ $R_3 = OH$ $R_4 = OH$ $R_5 = OAc$
epoxytaccalonolide L: $R_1 = OAc$ $R_2 = H$ $R_3 = OH$ $R_4 = OC(O)CH_2OH$ $R_5 = OAc$
epoxytaccalonolide N: $R_1 = OAc$ $R_2 = H$ $R_3 = OH$ $R_4 = H$ $R_5 = OH$
epoxytaccalonolide G: $R_1 = OAc$ $R_2 = OH$ $R_3 = OH$ $R_4 = H$ $R_5 = H$
epoxytaccalonolide R: $R_1 = OAc$ $R_2 = OH$ $R_3 = OAc$ $R_4 = H$ $R_5 = OAc$
epoxytaccalonolide S: $R_1 = $ isobutyrate $R_2 = H$ $R_3 = OH$ $R_4 = H$ $R_5 = OAc$
epoxytaccalonolide T: $R_1 = $ 3-methylbutanoate $R_2 = OH$ $R_3 = OAc$ $R_4 = H$ $R_5 = OAc$
epoxytaccalonolide U: $R_1 = OH$ $R_2 = OH$ $R_3 = OAc$ $R_4 = H$ $R_5 = OAc$
epoxytaccalonolide Z: $R_1 = OAc$ $R_2 = OH$ $R_3 = OH$ $R_4 = R_5 = OAc$
epoxytaccalonolide AA: $R_1 = OAc$ $R_2 = OH$ $R_3 = R_4 = R_5 = OAc$
epoxytaccalonolide AB: $R_1 = OAc$ $R_2 = OH$ $R_3 = OH$ $R_4 = OAc$ $R_5 = OH$
epoxytaccalonolide AG: $R_1 = $ 3-methylbutanoate $R_2 = OH$ $R_3 = OH$ $R_4 = H$ $R_5 = OAc$
epoxytaccalonolide AH: $R_1 = $ 3-methylbutanoate $R_2 = H$ $R_3 = OH$ $R_4 = H$ $R_5 = OAc$
epoxytaccalonolide AI: $R_1 = $ 3-methylbutanoate $R_2 = H$ $R_3 = OH$ $R_4 = H$ $R_5 = OH$
epoxytaccalonolide AL: $R_1 = OAc$ $R_2 = OH$ $R_3 = OH$ $R_4 = H$ $R_5 = OH$
epoxytaccalonolide AM: $R_1 = $ 3-methylbutanoate $R_2 = OH$ $R_3 = OH$ $R_4 = H$ $R_5 = OH$
epoxytaccalonolide AN: $R_1 = OH$ $R_2 = H$ $R_3 = OH$ $R_4 = H$ $R_5 = OH$
epoxytaccalonolide AP: $R_1 = OAc$ $R_2 = OH$ $R_3 = OH$ $R_4 = H$ $R_5 = OAc$

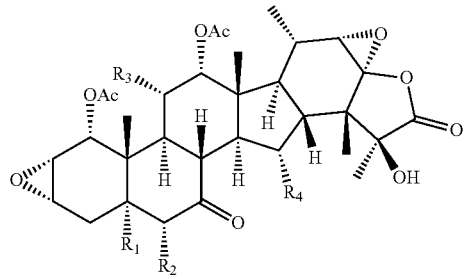

epoxytaccalonolide I: R₁ = H    R₂ = OH    R₃ = OAc    R₄ = OH
epoxytaccalonolide J: R₁ = H    R₂ = OH    R₃ = OAc    R₄ = OAc
epoxytaccalonolide K: R₁ = OH   R₂ = OH    R₃ = OAc    R₄ = OH
epoxytaccalonolide M: R₁ = OH   R₂ = OH    R₃ = H      R₄ = oxo

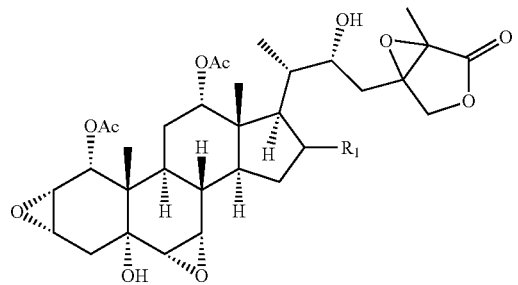

epoxytaccalonolide O: R₁ = β-OH
epoxytaccalonolide P: R₁ = oxo

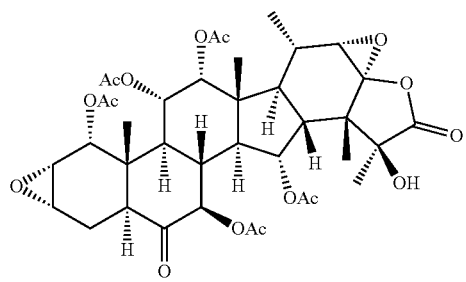

epoxytaccalonolide V

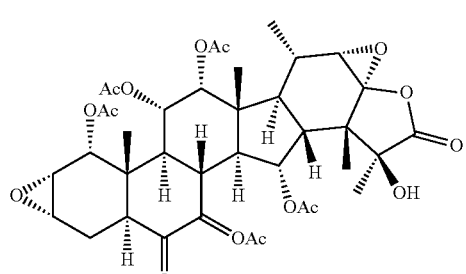

epoxytaccalonolide H

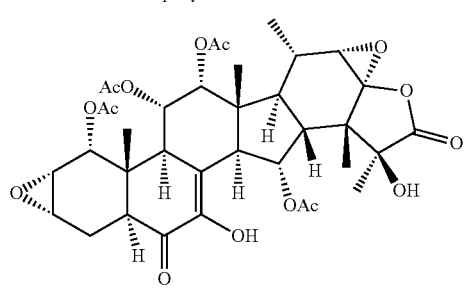

epoxytaccalonolide H2

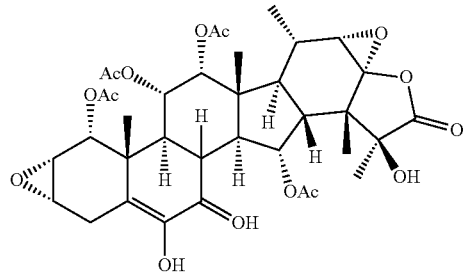

epoxytaccalonolide AD

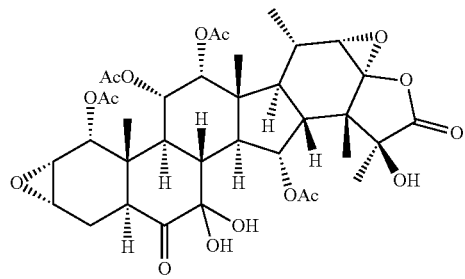

epoxytaccalonolide AE

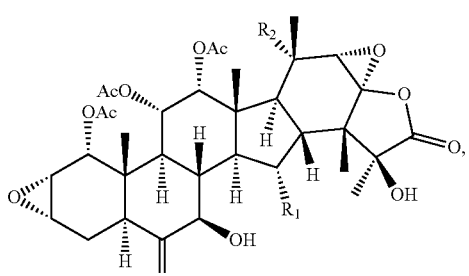

epoxytaccalonolide W: R₁ = OH   R₂ = OH
epoxytaccalonolide AC: R₁ = OAc  R₂ = OOH

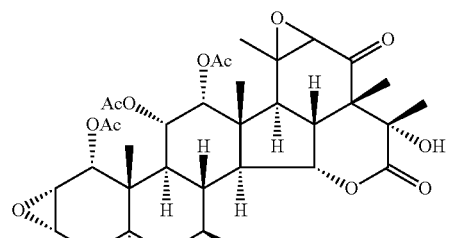

epoxytaccalonolide X

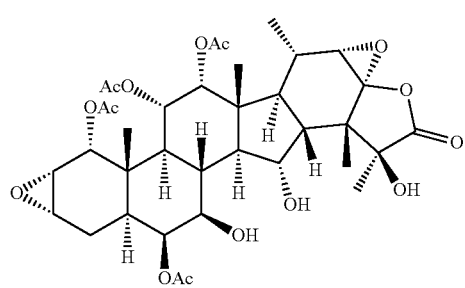

epoxy-TA-NaBH4-12

-continued

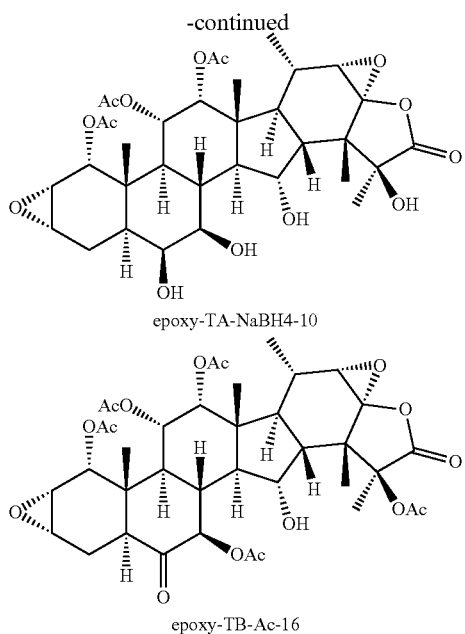

epoxy-TA-NaBH4-10 epoxy-TB-Ac-16 or pharmaceutically acceptable salts thereof.

The compound may be a mixture of epoxytaccalonolides (defined as a taccalonolide with 1 C22,23-epoxyl group), which contains two or more multiple compounds in any ratio with structures represented by the above formulae. The mixture of epoxytaccalonolides may be produced by epoxidation of a crude extract of the roots and/or rhizomes of the *Tacca* species, including but not limited to, *T. chantrieri, T. integrifolia, T plantaginea, T. pinnatifida leontopetaloides*, and *T. cristata aspera*.

The hyperproliferative cell may be a solid tumor cancer cell, such as a lung cancer cell, a brain cancer cell, a head and neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a prostate cancer cell, a skin cancer cell, an oral cancer cell or a esophageal cancer cell. The cancer cell may alternatively be a leukemia, lymphoma, or myeloma cell, such as an acute myeloid leukemia, chronic myelogenous leukemia or multiple myeloma. The hyperproliferative mammalian cell might be an endothelial or smooth muscle cell that lines blood vessels or a cell of the skin such as an epidermal cell or melanocyte.

The hyperproliferating cell may be located in a subject, such as a human subject. The method may then further comprising administering to said subject a second therapy, such as chemotherapy, radiotherapy, immunotherapy, toxin therapy, hormone therapy, gene therapy or surgery. The second therapy may be given at the same time as said compound, or before or after said compound.

The present invention also provides a mixture of epoxytaccalonolides (defined as a taccalonolide with a C22,23-epoxyl group), which contains two or more compounds in any ratio with structures represented by the above formulae. The mixture of epoxytaccalonolides may be produced by epoxidation of a crude extract of the roots and/or rhizomes of the *Tacca* species, including but not limited to, *T. chantrieri, T. integrifolia, T plantaginea, T. pinnatifida leontopetaloides*, and *T. cristata aspera*.

C. Chemical Group Definitions

When used in the context of a chemical group, "hydrogen" means —H; "hydroxy" means —OH; "hydroperoxy" means —OOH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

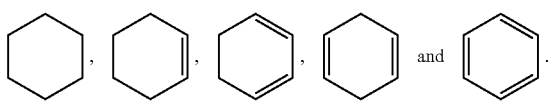

As will be understood by a person of skill in the art, no one such ring atom forms part of more than one double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "▬◀" means a single bond where the group attached to the thick end of the wedge is "out of the page." The symbol "⫼⫼⫼" means a single bond where the group attached to the thick end of the wedge is "into the page". The symbol "⌇" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

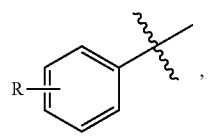

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

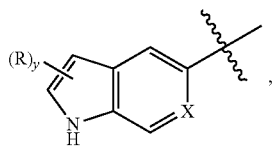

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C≤10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, A, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CHF, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHC$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

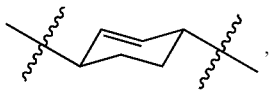 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl) phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

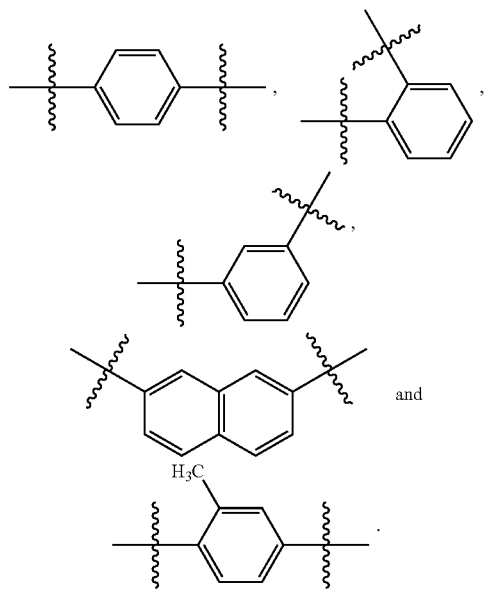

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

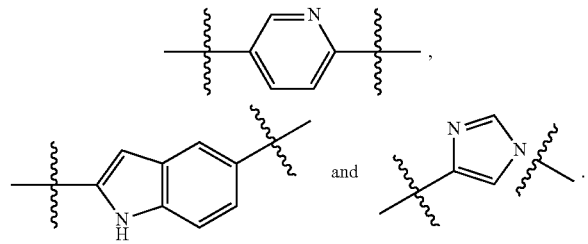

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

As used herein, a "chiral auxiliary" refers to a removable chiral group that is capable of influencing the stereoselectivity of a reaction. Persons of skill in the art are familiar with such compounds, and many are commercially available.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes"

one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylprop ionic acid, 4,4'-methylenebis β-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

D. Isolation and Semisynthesis

Methods for isolating and generating taccalonolide compounds by semi-synthesis according to the present invention are provided by the examples. Those of skill in the art would recognize similar methodologies that may also be employed.

II. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render agents stable and allow for uptake by target cells. Aqueous compositions of the present invention comprise an effective amount of the compounds, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, dermal, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Proliferative Diseases

The present invention also involves, in one embodiment, the treatment of a hyperproliferative mammalian cell including a cancer cell. It is contemplated that a wide variety of tumors may be treated using taccalonolide therapy, including cancers of the brain, lung, liver, spleen, kidney, lymph node, pancreas, small intestine, blood cells, colon, stomach, breast, endometrium, prostate, testicle, ovary, uterus, skin, head and neck, esophagus, bone marrow, blood or other tissue. Other mammalian cells exhibiting a hyperproliferative phenotype including vascular or skin epidermal cells may be treated with a taccalonolide therapy.

It is not necessary that the cell be killed or induced to undergo normal cell death or "apoptosis." Rather, to accomplish a meaningful treatment, all that is required is that the growth be slowed to some degree. It may be that the cell growth is completely blocked, however, or that some regression is achieved. Clinical terminology such as "remission" and "reduction of tumor" burden also are contemplated given their normal usage. Also, rendering a non-resectable tumor resectable may also be a useful clinical endpoint. Even the elongation of patient life, or reduction of patient discomfort (improving quality of life) is a goal of the present invention and thus helps define treatment.

C. Treatment Methods

Compounds that stabilize microtubules are generally useful as anti-cancer compounds and in the treatment of vascular diseases lining vascular stents. They can be administered to mammalian subjects (e.g., human patients) alone or in conjunction with other drugs that treat cancer or other hyperproliferative diseases.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2, 3, 4, 6, 8, 10, 20, 50, 100, 150, or more times). Encapsulation of the taccalonolide in a suitable delivery vehicle (e.g., polymeric microparticles or implantable devices) may increase the efficiency of delivery, particularly for oral delivery.

D. Stents

The present compounds may also be used as a coating on or impregnated into a stent. The anti-proliferative capacity of these compounds may find advantageous application in the treatment of vascular stenosis occurring subsequent to treatments involving stent placement.

A particular type of stent is a coronary stent. Coronary stents are effectively tubes placed in the coronary arteries to keep the arteries open in the treatment of coronary heart disease. It is often used in a procedure called percutaneous coronary intervention (PCI). Stents reduce chest pain and have been shown to improve survivability in the event of an acute myocardial infarction, but may suffer from restenosis, where the stent itself serves as a platform for narrowing the artery. The compounds of the present invention would be utilized to prevent cell proliferation in and around the stent, thereby reducing or slowing restenosis. Similar stents and procedures are used in non-coronary vessels, e.g., in the legs in peripheral artery disease.

E. Combination Therapies

It is common in many fields of medicine to treat hyperproliferative diseases including cancer with multiple therapeutic modalities, often called "combination therapies." To treat hyperproliferative diseases using the methods and compositions of the present invention, one would generally contact a target cell or subject with a taccalonolide according to the present invention and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes a taccalonolide according to the present invention and the other includes the other agent.

Alternatively, a taccalonolide according to the present invention may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either a taccalonolide according to the present invention or the other therapy will be desired. Various combinations may be employed, where the taccalonolide according to the present invention is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated. The skilled artisan is directed to "Remingtons Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are contemplated for use with in combination with taccalonolides of the present invention. For example, selective estrogen receptor antagonists; ("SERMs"), such as tamoxifen, 4-hydroxy tamoxifen (Nolvadex), fulvestrant (Falsodex), raloxifene (Evista); aromatase inhibitors including anastrozole (Arimidex), exemestane (Aromasin) and letrozole (Femara); antiandrogens including flutamide (Eulexin) and bicalutamide (Casodex).

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a taccalonolide, as described above.

Heat shock protein 90 is a regulatory protein found in many eukaryotic cells. HSP90 inhibitors have been shown to be useful in the treatment of cancer. Such inhibitors include geldanamycin, 17-(Allylamino)-17-demethoxygeldanamycin, PU-H71 and Rifabutin.

Agents that directly cross-link DNA or form adducts are also envisaged. Agents such as cisplatin, carboplatin and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include doxorubicin (Adriamycin), etoposide, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the semi-synthesis of material derived from plants of the genus *Taxus*, and include paclitaxel, docetaxel and cabazitaxel. Other microtubule inhibitors include the epothilones, *Vinca* alkaloids or eribulin (Havalin).

mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy uses TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used. Other antimetabolites include methotrexate, premetrexed, 6-mercaptopurine, dacarbazine, fludarabine, capecitabine, gemcitabine and decitabine.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of a taccalonolide according to the present invention to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining a taccalonolide according to the present invention with chemo- and radiotherapies, it also is contemplated that combination with immunotherapy, hormone therapy, toxin therapy and surgery. In particular, one may employ targeted therapies such as bevacizumab (Avastin), cetuximab (Erbitux), imatinib (Gleevec), transtuzumab (Herceptin) and rituximab (Rituxan).

It also should be pointed out that any of the foregoing therapies may prove useful by themselves in treating cancer.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Instrumentation.

NMR spectra were recorded on a Bruker Avance 600 or 700 MHz instrument equipped with a cryogenically cooled probe. All spectra were measured and reported in ppm using the residual solvent ($CDCl_3$) as an internal standard. The HRMS was measured using a Thermo Scientific LTQ Orbitrap mass spectrometer. IR data were obtained on a Bruker Vector 22 with a Specac Golden Gate ATR sampler. The UV spectra were measured on a Varian Cary 5000 UV-Vis NIR spectrophotometer. TLC was performed on aluminum sheets (silica gel 60 $F_{254}$, Merck KGaA, Germany). HPLC was performed on a Waters Breeze HPLC system. LC/MS was conducted on a Waters Alliance 2695 HPLC module, 996 photodiode array detector, and Micromass Quattro triple quadrupole mass spectrometer equipped with ESI. The purities of all compounds were determined to be greater than 95% by LC/MS and NMR.

Plant Material.

*Tacca chantreiri* and *T. integrifolia* plants were purchased from a commercial grower. The roots and rhizomes were collected from living plants and stored at −20° C. until lyophilized.

Extraction and Isolation of Taccalonolide Z.

The roots and rhizomes of *T. integrifolia* (1445 g) were extracted using supercritical fluid $CO_2$ with methanol and nonpolar lipids were removed by hexane extraction. The material was further extracted with $CH_2Cl_2$ to yield 11.7 grams of extract. The $CH_2Cl_2$ extract was purified by silica gel flash chromatography followed by repeated normal phase HPLC to yield 13.1 mg of taccalonolide Z. Taccalonolide Z was obtained as a white powder. The proton NMR spectrum showed four acetyl signals at δ 2.16, 2.13, 2.00, 1.97, five methyl signals at δ 1.64 (s), 1.34 (s), 0.98 (s), 0.89 (d, J=7.2 Hz), 0.73 (s), five oxygenated methine signals at δ 5.53 (t, J=10.2 Hz), 5.23 (br), 5.22 (dd, J=9.6, 2.4 Hz), 4.85 (d, J=5.4 Hz), 4.73 (dd, J=10.2, 5.4 Hz), two epoxy methine signals at δ 3.74 (t, J=4.5 Hz) and 3.61 (dt, J=4.2, 1.8 Hz), one olefinic signal at δ 5.06 (d, J=1.2 Hz). All these proton NMR data are similar to those of taccalonolide A and indicated that taccalonolide Z is a taccalonolide type steroid. The molecular formula of $C_{36}H_{46}O_{15}$ was determined by HRMS of 719.2934 (calcl 719.2915), suggesting that taccalonolide Z has one more oxygen than taccalonolide A. In addition, three signals for hydroxyl groups were observed at δ 3.64 (s), 3.45 (d, J=5.4 Hz), and 2.58 (s), which is one more than taccalonolide A. The carbon-13 NMR showed 7 oxygenated carbon signals at δ 79.08, 78.74, 74.13, 74.06, 71.20, 71.17, 71.14, and confirmed one more hydroxyl group for taccalonolide Z as compared to taccalonolide A. The $^3J$ HMBC correlation between the hydroxyl proton signal at δ 3.64 and the carbonyl carbon at δ 208.34 (C-6) suggested that the hydroxyl group is located at C-5. The configuration of this hydroxyl group was determined as a by the NOE correlations between 5-OH/H-7,9,4α. The other $^1H$ and $^{13}C$ NMR data for taccalonolide Z is similar to those for taccalonolide A, thus, taccalonolide Z was determined as 5α-hydroxy-taccalonolide A and this was confirmed by 2D NMR data. A trivial name taccalonolide Z was given to this compound.

Taccalonolide Z:

white powder; ESIMS: m/z 719.4 $[M+H]^+$, 736.4 $[M+NH_4]^+$, 731.5 $[M+Na]^+$; $^1H$ NMR: δ (ppm) 5.53 (t, J=9.8 Hz, H-15), 5.23 (br., H-12), 5.22 (dd, J=9.6, 2.4 Hz, H-11), 5.06 (d, J=1.5 Hz, H-22), 4.85 (d, J=5.4 Hz, H-1), 4.73 (dd, J=10.2, 5.1 Hz, H-7), 3.74 (t, J=4.5 Hz, H-2), 3.64 (s, 5-OH), 3.61 (m, H-3), 3.45 (d, J=5.2 Hz, 7-OH), 3.17 (t, J=11.6 Hz, H-9), 2.58 (s, 25-OH), 2.57 (dd, J=15.0, 1.6 Hz, H-4a), 2.52 (t, J=10.1 Hz, H-14), 2.42 (dd, J=13.4, 10.2 Hz, H-16), 2.23 (d, J=16.7 Hz, H-4b), 2.16 (s, 3H, 1-OAc), 2.15 (m, H-20), 2.13 (s, 3H, 12-OAc), 2.00 (s, 3H, 15-OAc), 1.97 (s, 3H, 11-OAc), 1.81 (dd, J=13.4, 9.8 Hz, H-17), 1.64 (s, 3H, H-27), 1.56 (q, J=10.8 Hz, H-8), 1.34 (s, 3H, H-28), 0.98 (s, 3H, H-18), 0.89 (d, 3H, J=7.2 Hz, H-21), 0.73 (s, 3H, H-19); $^{13}C$ NMR: δ (ppm) 208.34 (C-6), 178.10 (C-26), 172.07 (15-OAc), 170.85 (11-OAc), 169.40 (1-OAc), 169.25 (12-OAc), 154.50 (C-23), 111.07 (C-22), 79.08 (C-5), 78.74 (C-25), 74.13 (C-12), 74.06 (C-1), 71.20 (C-15), 71.17 (C-7), 71.14 (C-11), 54.16 (C-14), 54.06 (C-3), 50.97 (C-16), 50.60 (C-2), 50.07 (C-24), 48.85 (C-17), 45.86 (C-10), 44.19 (C-8), 43.15 (C-13), 37.13 (C-9), 30.61 (C-20), 26.94 (C-4), 25.32 (C-28), 22.36 (15-OAc), 21.16 (11-OAc), 21.02 (12-OAc), 20.72 (1-OAc), 20.61 (C-27), 20.08 (C-21), 14.61 (C-19), 13.37 (C-18).

Extraction and Isolation of the Taccalonolides A, E, AA, T and R.

Dried and pulverized rhizomes (2.3 kg) of *T. chantrieri* were extracted in several batches using supercritical $CO_2$ with MeOH. The crude extracts were washed with hexanes and extracted with $CH_2Cl_2$. The $CH_2Cl_2$ extracts were subjected to silica gel flash chromatography and eluted with hexanes: isopropanol (82:18) to obtain the taccalonolide enriched fraction. This fraction (1.4 g) was further purified on a silica gel HPLC column and eluted with isooctane:isopropanol (81:19) to yield fractions 1-8. Taccalonolides A and E were obtained from fractions 2 and 4 respectively. Fraction-1 (33 mg) was separated on a C-18 HPLC column, eluting with a gradient of acetonitrile:$H_2O$ from 30% to 80% over 40 minutes, to yield 1.2 mg of taccalonolide AA and 0.8 mg of taccalonolide T. Fraction-3 was purified on silica gel flash column and eluted with $CH_2Cl_2$:acetone 85:15 to yield taccalonolide R.

Taccalonolide AA was isolated as a white powder. The proton NMR spectrum of taccalonolide AA showed characteristics almost identical to taccalonolide Z, indicating a similar taccalonolide structure. Five acetyl signals at δ 2.20, 2.15, 2.14, 2.00, 1.98, five methyl signals at δ 1.64 (s), 1.34 (s), 1.04 (s), 0.91 (d, J=7.0 Hz), 0.72 (s), five acetoxylated methine signals at δ 5.72 (d, J=11.0 Hz), 5.55 (d, J=9.5 Hz), 5.25 (br), 5.23 (brd, J=11.0 Hz), 4.91 (d, J=5.0 Hz), two epoxyl methine signals at δ 3.72 (t, J=4.5 Hz) and 3.59 (br), one olefinic signal at δ 5.09 (br). Taccalonolide AA has one more acetyl signal than taccalonolide Z. The chemical shift of H-7 at δ 5.72 (d, J=11.0 Hz) was approximately 0.99 ppm down-field than that of taccalonolide Z, suggesting this additional acetyl group was located at 7-OH. An HMBC correlation between H-7 and a carbonyl carbon at δ 170.8 confirmed this assignment. The other $^1H$, $^{13}C$ and 2D NMR data are similar to 5, thus, the structure of taccalonolide AA was determined and a trivial name taccalonolide AA was assigned.

Taccalonolide AA:

white powder; ESIMS: m/z 761.4 $[M+H]^+$, 778.4 $[M+NH_4]^+$, 783.5 $[M+Na]^+$, 701.3 $[M-OAc]^+$; $^1H$ NMR: δ (ppm) 5.73 (d, J=11.0 Hz, H-7), 5.55 (t, J=9.4 Hz, H-15), 5.25 (d, J=2.6 Hz, H-12), 5.23 (dd, J=11.7, 2.6 Hz, H-11), 5.09 (d, J=1.4 Hz, H-21), 4.91 (d, J=5.5 Hz, H-1), 3.72 (t, J=4.5 Hz, H-2), 3.61 (s, 5-OH), 3.59 (m, H-3), 3.30 (t, J=11.4 Hz, H-9), 2.63 (t, J=10.0 Hz, H-14), 2.62 (s, 25-OH), 2.56 (brd, J=14.5 Hz, H-4a), 2.43 (dd, J=13.4, 9.8 Hz, H-16), 2.20 (s, 3H, 1-OAc), 2.19 (m, H-4b), 2.17 (m, H-20), 2.16 (s, 3H, 11-OAc), 2.15 (s, 3H, 12-OAc), 2.03 (q, J=11.0 Hz, H-8), 2.00 (s, 3H, 7-OAc), 1.98 (s, 3H, 15-OAc), 1.65 (s, 3H, H-27), 1.33 (s, 3H, H-28), 1.04 (s, 3H, H-18), 0.92 (s, 3H, H-21), 0.73 (s, 3H, H-18); $^{13}C$ NMR: δ (ppm) 201.65 (C-6), 178.04 (C-25), 172.10 (15-OAc), 170.88 (11-OAc), 170.76 (7-OAc) 169.51 (1-OAc), 169.33 (12-OAc), 154.34 (C-23), 111.33 (C-22), 79.76 (C-5), 79.10 (C-26), 74.31 (C-7), 74.26 (C-1), 73.99 (C-12), 71.54 (11), 71.22 (C-15), 54.34 (14), 54.22 (C-3), 51.60 (C-16), 50.60 (C-2), 50.26 (C-24), 48.66 (C-17), 45.64 (C-10), 43.61 (C-13), 39.48 (C-8), 38.57 (C-9), 30.75 (C-20), 26.78 (C-4), 25.37 (C-28), 22.79 (15-OAc), 21.27 (7-OAc), 21.23 (12-OAc), 21.19 (11-OAc), 20.97 (1-OAc), 20.68 (C-21), 20.21 (C-27), 14.88 (C-19), 13.74 (C-18).

Extraction and Isolation of Taccalonolides A, B, AC, AD, AE, AF.

The roots and rhizomes of *Tacca plantaginea* were extracted with ethanol. The extract was subjected to silica gel column chromatography to generate a taccalonolide A fraction. This fraction (372.02 mg) was separated by column chromatography (Biotage) using HP silica and eluted with a gradient of $CHCl_3$:acetone yielding ten fractions. Taccalonolide B (5.95 mg) was obtained from fraction 4. Fraction 5 (252.92 mg) was subjected to HPLC purification and eluted with a gradient of acetonitrile:$H_2O$, yielding taccalonolide A, B and AE. Fraction 7 (20.51 mg) was purified using the same procedure yielding taccalonolide A (12.21 mg), B (0.33 mg), AE (1.39 mg), AD (2.29 gm) and AF (0.69 mg). Fraction 9 (5.25 mg) afforded taccalonolide H1 (0.89 mg), AD (0.92 mg), AE (1.02 mg) and AF (0.28 mg) after HPLC purification.

Taccalonolide AC:

ESIMS: 717 $[M+H-H_2O]^+$, 752 $[M+NH_4]^+$. $^1H$ NMR: δ (ppm) 5.71 (s, H-22), 5.49 (t, J=9.0 Hz, H-15), 5.29 (d, J=2.7 Hz, H-12), 5.27 (dd, J=12.0, 2.7 Hz, H-11), 4.77 (d, J=5.8 Hz, H-1), 4.03 (dd, J=10.6, 4.4 Hz, H-7), 3.86 (d, J=4.4 Hz, 7-OH), 3.49 (dd, J=5.6, 3.1 Hz, H-2), 3.38 (m), 2.78 (dd, J=10.8, 4.1 Hz, H-5), 2.75 (t, J=11.6 Hz, H-9), 2.62 (m, H-16), 2.61 (s, 25-OH), 2.60 (m, H-17), 2.41 (t, J=10.4 Hz, H-14), 2.24 (m, $H_2$-4), 2.18 (s, 3H, 1-OAc), 2.10 (s, 3H, 12-OAc) 2.01 (s, 6H, 11,15-OAc), 1.75 (m, H-8), 1.72 (s, 3H, H-27), 1.38 (s, 3H, H-21), 1.35 (s, 3H, H-28), 1.10 (s, 3H, H-18), 0.77 (s, 3H, H-19). $^{13}C$ NMR: δ (ppm) 210.0 (C-6), 178.1 (C-26), 172.4 (15-OAc), 170.8 (11-OAc), 170.0 (12-OAc), 169.6 (1-OAc), 153.9 (C-23), 112.1 (C-22), 84.5 (C-20), 79.4 (C-25), 74.8 (C-7), 73.8 (C-12), 72.8 (C-1), 71.0 (C-15), 70.9 (C-11), 53.8 (C-14), 52.3 (C-3), 50.3 (C-24), 49.6 (C-2), 46.4 (C-17), 45.5 (C-16), 43.8 (C-13), 43.2 (C-8), 42.8 (C-10), 42.2 (C-5), 40.1 (C-9), 25. (C-28), 21.9 (11, 15-OAc), 21.7 (C-4), 21.2 (12-OAc), 20.6 (1-OAc), 20.6 (C-21), 20.4 (C-27), 15.2 (C-18), 13.0 (C-19).

Taccalonolide AD:

ESIMS: 701 $[M+H]^+$, 718 $[M+NH_4]^+$, 723 $[M+Na]^+$. $^1H$ NMR: δ (ppm) 6.26 (s, 6-OH), 5.74 (dd, J=9.7, 8.7 Hz, H-15), 5.46 (dd, J=11.3, 3.3 Hz, H-11), 5.35 (d, J=3.3 Hz, H-11), 5.10 (d, J=1.4 Hz, H-22), 4.95 (d, J=5.5 Hz, H-1), 3.56 (dd, J=5.5, 4.0 Hz, H-2), 3.42 (brt, J=3.8 Hz, H-3), 3.36 (d, J=19.8 Hz, H-4), 2.88 (t, J=12.2 Hz, H-9), 2.63 (dd, J=19.8, 4.2 Hz, H-4), 2.62 (d, J=12.0 Hz, H-8), 2.57 (s, 25-OH), 2.48 (m, H-13), 2.47 (m H-16), 2.24 (m, H-20), 2.15 (15-OAc), 2.13 (1-OAc), 2.08 (12-OAc), 2.02 (11-OAc), 1.77 (dd, J=13.6, 10.0 Hz, H-17), 1.61 (s, 3H, H-27), 1.34 (s, 3H, H-28), 1.22 (s, 3H, H-19), 1.04 (s, 3H, H-18), 0.97 (d, 3H, J=7.1 Hz, H-21). $^{13}C$ NMR: δ (ppm) 190.3 (C-7), 178.6 (C-26), 172.5 (15-OAc), 170.6 (11-OAc), 169.7 (1-OAc), 169.4 912-OAc), 154.2 (C-23), 143.9 (C-6), 127.3 (C-5), 111.1 (C-22), 79.3 (C-25), 72.4 (C-12), 71.7 (C-1), 70.1 (C-15), 69.5 (C-11), 51.1 (C-16), 50.7 (C-24), 49.6 (C-3), 49.1 (C-14), 48.6 (C-2), 47.5 (C-17), 43.8 (C-13), 40.0 (C-8), 38.7 (C-10), 38.1 (C-9), 30.3 (C-20), 24.5 (C-28), 23.3 (C-4), 22.7 (15-OAc), 21.1 (11-)Ac), 20.5 (12-OAc), 20.3 (1-OAc), 20.0 (C-27), 19.9 (C-21), 16.7 (C-19), 12.7 (C-18).

Taccalonolide AE:

ESIMS: 719 $[M+H]^+$, 736 $[M+NH_4]^+$, and 741 $[M+Na]^+$. $^1H$ NMR: δ (ppm) 5.60 (t, J=10.1 Hz, H-15), 5.30 (dd, J=11.6, 2.9 Hz, H-11), 5.27 (d, J=2.9 Hz, H-12), 5.10 (d, J=2.1 Hz, H-22), 5.01 (s, 7-OH), 4.73 (d, J=6.0 Hz, H-1), 3.64 (s, 7-OH), 3.48 (t, J=5.6, 4.2 Hz, H-2), 3.38 (m, H-4), 3.30 (dd, J=10.7, 5.0 Hz, H-5), 2.89 (t, J=12.0 Hz, H-9), 2.66 (t, J=10.1 Hz, H-15), 2.66 (dd, J=11.0, 9.6 Hz, H-14), 2.59 (s, 25-OH), 2.46 (dd, J=13.2, 10.7 Hz, H-16), 2.21 (m, H-20), 2.18 (m, H-4), 2.19 (s, 1-OAc), 2.14 (s, 12-OAc), 2.07 9s, 15-OAc), 2.00 (s, 11-OAc), 1.85 (m H-17), 1.83 (m, H-8), 1.65 (s, 3H, H-27), 1.35 (s, 3H, H-28), 1.03 (s, 3H, H-18), 0.94 (d, 3H, J=7.0 Hz, H-21), 0.79 (s, 3H, H-19). $^{13}$C NMR: δ (ppm) 206.7 (C-6), 178.0 (C-26), 171.0 (15-OAc), 170.8 (11-OAc), 169.7 (1-OAc), 169.3 (12-OAc), 154.4 (C-23), 111.4 (C-22), 92.4 (C-7), 79.1 (C-25), 73.8 (C-12), 72.8 (C-1), 72.5 (C-15), 70.8 (C-11), 52.2 (C-3), 51.1 (C-16), 49.8 (C-24), 49.6 (C-2), 49.1 (C-17), 48.4 (C-14), 44.2 (C-8), 43.2 (C-13), 42.7 (C-10), 39.6 (C-5), 39.2 (C-9), 30.9 (C-20), 25.3 (C-28), 22.4 (15-OAc), 21.5 (C-4), 21.2 (11-oaC), 20.9 (12-oaC), 20.7 (C-27), 20.6 (1-OAc), 20.0 (C-21), 13.4 (C-18), 12.5 (C-18).

Taccalonolide AF:

ESIMS: 719 [M+H]$^+$, 736 [M+NH$_4$]$^+$, and 741 [M+Na]$^+$. $^1$H NMR: δ (ppm) 5.52 (t, J=9.4 Hz, H-15), 5.28 (dd, J=11.4, 2.7 Hz, H-11), 5.20 (d, J=2.7 Hz, H-12), 4.74 (d, J=5.5 Hz, H-1), 3.98 (dd, J=11.0, 4.1 Hz, H-7), 3.85 (d, J=4.1 Hz, 7-OH), 3.48 (ddt, J=5.6, 3.5 Hz, H-1), 3.39 (m, H-3), 3.29 (s, H-22), 2.76 (m, H-5), 2.71 (t, J=11.0 Hz, H-9), 2.69 (s, 25-OH), 2.43 (dd, J=11.4, 9.0 Hz, H-14), 2.21 (m, H-4), 2.19 (s, 3H, 1-OAc), 2.16 (s, 3H, 12-OAc), 2.07 (m, H-16), 2.03 (t, J=9.6 Hz, H-17), 2.02 (s, 3H, 15-OAc), 2.00 (s, 3H, 11-OAc), 1.76 (s, 3H, H-27), 1.35 (s, 3H, H-28), 1.03 (d, J=7.9 Hz, 3H, H-21), 0.88 (s, 3H, H-18), 0.78 (s, 3H, H-19). $^{13}$C NMR: δ (ppm) 209.9 (C-6), 177.4 (C-26), 171.6 (15-OAc), 170.5 (11-OAc), 169.4 (1-OAc), 169.0 (12-OAc), 92.2 (C-23), 79.6 (C-25), 75.7 (C-7), 74.0 (C-12), 73.1 (C-1), 71.6 (C-15), 71.2 (C-11), 65.9 (C-22), 54.6 (C-14), 52.9 (C-3), 49.9 (C-2), 48.1 (C-16), 46.8 (C-24), 45.2 (C-17), 43.7 (C-13), 43.4 (C-8), 43.2 (C-10), 42.6 (C-5), 40.3 (C-9), 32.1 (C-20), 24.1 (C-27), 22.9 (15-OAc), 21.8 (C-4), 21.4 (11-OAc), 21.0 (12-OAc), 20.3 (1-OAc), 20.1 (C-28), 19.1 (C-21), 13.6 (C-18), 13.5 (C-19).

Extraction and Isolation of the Taccalonolides B and AI.

Dried and pulverized rhizomes of *T. chantrieri* were extracted in several batches using supercritical $CO_2$ with MeOH. The crude extracts were washed with hexanes and extracted with $CH_2Cl_2$. The $CH_2Cl_2$ extracts were subjected to silica gel flash chromatography and eluted with hexanes:isopropanol (82:18) to obtain the taccalonolide enriched fraction. This fraction was further purified on a silica gel HPLC column and eluted with isooctane:isopropanol (81:19) to yield fractions 1-8. Fraction 2 was hydrolyzed with 0.05 M sodium bicarbonate at room temperature for 40 h. The solution was stirred at room temperature for 44 h. The reaction solution was extracted with EtOAc and purified on HPLC to yield taccalonolide B as the major product and taccalonolide AI as a minor compound.

Taccalonolide AI was obtained as a white powder. The ESI-MS showed the protonated molecular ion at m/z 645.4 [M+H]$^+$. The proton NMR spectrum showed only one acetyl signal at δ 2.08. This acetoxyl group was assigned to C-12 by the chemical shift of H-12 at 4.99 (t, J=2.7 Hz) and the HMBC correlation of this proton with the acetyl carbon. The chemical shift of H-15 at 4.38 (dt, J=11.2, 2.8 Hz) indicated a hydroxyl group at C-15. A 3-methylbutanoate was suggested by signals for two methyl group at 1.01 (d, J=6.1 Hz) and 1.00 (d, J=6.1 Hz) and confirmed by COSY and HSQC spectra. The correlations between H-1 at 4.59 and the carbonyl carbon at 171.8 located the 3-methylbutanoate at C-1. The other signals of taccalonolide AI are similar to taccalonolide N. Thus the structure of taccalonolide AI was determined as depicted. (FIG. 1)

Taccalonolide AI:

white powder; ESIMS: m/z 645.4 [M+H]$^+$, 662.3 [M+NH$_4$]$^+$, 667.5 [M+Na]$^+$, 599.3, 567.3, 557.2, 539.3, 521.2, 497.3; $^1$H NMR (500 MHz, CDCl$_3$) δ 5.23 (d, J=2.6 Hz, 15-OH), 5.01 (br, H-22), 4.99 (t, J=2.7 Hz, H-12), 4.72 (s, 25-OH), 4.59 (d, J=5.2 Hz, H-1), 4.45 (br, 7-OH), 4.38 (dt, J=11.2, 2.8 Hz, H-15), 4.01 (d, J=10.3 Hz, H-7), 3.55 (t, J=5.8 Hz, H-2), 3.40 (br, H-3), 2.70 (dd, J=11.3, 4.5 Hz, H-5), 2.39 (dd, J=13.1, 10.9 Hz, H-6), 2.28 (dd, J=15.3, 4.3 Hz, H-4), 2.21 (m, H-20), 2.17 (m, H-4), 2.15 (m, H-9), 2.14 (m, CH$_2$ of 3-methylbutanoate), 2.13 (m, CH of 3-methylbutanoate), 2.11 (m. H-14), 2.08 (s, 12-OAc), 1.99 (dd, J=10.1, 13.5 Hz, H-17), 1.72 (m, H-8), 1.70 (m, H-11), 1.67 (s, H-27), 1.37 (s, H-28), 1.01 (d, J=6.1 Hz, CH$_3$ of 3-methylbutanoate), 1.00 (d, J=6.1 Hz, CH$_3$ of 3-methylbutanoate), 0.95 (d, J=7.2 Hz, H-21), 0.82 (s, H-18), 0.76 (s, H-19).

Extraction and Isolation of Taccalonolides AG and AH.

The taccalonolides AG and AH were isolated from the roots of *Tacca chantrieri*. Freeze-dried material was ground to a fine powder and extracted with $CO_2$ and methanol using a supercritical fluid extractor. Non-polar lipids were removed by hexane extraction. The taccalonolides were further enriched by extraction with dichloromethane and water and the resultant fraction dried by evaporation. The crude taccalonolide extract was fractionated by flash chromatography on a silica column with hexanes and isopropanol. High performance liquid chromatography (HPLC) was used to separate the taccalonolides A and E. The HPLC fractions that eluted between A and E were combined and further fractionated by flash chromatography using a mixture of methylene chloride:acetone to generate 87 fractions. Fraction 29 was further separated by HPLC using a mixture of water:acetonitrile and a C18 Phenomenex large column. Fraction 18 contained an unresolvable mixture of taccalonolides AG and AH.

Taccalonolide AG:

ESIMS: 703 [M+H]$^+$, 720 [M+NH$_4$]$^+$, and 725 [M+Na]$^+$. $^1$H NMR: δ (ppm) 5.51 (t, J=9.5 Hz, H-15), 5.11 (br, H-22), 5.03 (br, H-12), 4.61 (d, J=5.9 Hz, H-1), 3.89 (d, J=10.1 Hz, H-7), 3.82 (Br, 7-OH), 3.54 (t, J=4.5 Hz, H-2), 3.39 (m, H-3), 2.67 (dd, J=10.7, 6.0 Hz, H-5), 2.41 (dd, J=12.9, 9.6 Hz, H-16), 2.37 (t, J=9.4 Hz, H-14), 2.23 (m, H-4), 2.22 (m, H-20), 2.17 (m, CH$_2$ of isovalerate), 2.16 (m, H-9), 2.15 (m, CH of isovalerate), 2.11 (s, 15-OAc), 2.00 (s, 12-OAc), 1.96 (dd, 13.3, 3.8), 1.75 (m, H-11), 1.73 (m, H-8), 1.66 (s, 3H, H-27), 1.37 (s, 3H, H-27), 1.03 (d, 6H, J=4.8 Hz, CH$_3$ of isovalerate), 0.98 (d, J=6.5 Hz, H-21), 0.87 (s, 3H, H-18), 0.70 (s, 3H, H-19). $^{13}$C NMR: δ (ppm) 210.2 (C-6), 178.2 (C-26), 172.1 (15-OAc), 171.7 (1-isovalerate), 169.1 (12-OAc), 154.7 (C-23), 111.5 (C-22), 77.0 (C-7), 74.1 (C-12), 72.0 (C-15), 71.1 (C-1), 54.8 (C-14), 52.9 (C-3), 51.4 (C-16), 50.1 (C-24), 49.7 (C-2), 48.8 (C-17), 43.8 (C-5), 43.7 (C-8), 43.4 (CH$_2$ of isovalerate), 37.3 (CH of isovalerate), 31.0 (C-20), 25.9 (C-9), 25.8 (C-28), 25.2 (C-11), 22.8 (12-OAc), 22.5 (CH$_3$ of isovalerate), 21.6 (C-4), 21.3 (15-OAc), 21.1 (C-27), 19.7 (C-21), 13.4 (C-18), 13.2 (C-19).

Isolation of taccalonolides AP, AQ and AR.

All the taccalonolides described in the literature were isolated from the roots and rhizomes of plants of the genus *Tacca*. In an attempt to identify new taccalonolides the petioles of *T. chantrieri* were investigated. The petioles were extracted three times with methanol and precipitated with methylene chloride. The supernatant was fractionated using silica flash chromatography with methylene chloride and methanol as solvents. 190 fractions were collected and combined based on their thin layer chromatography profiles. Fractions 85-89 were combined and subjected to another round of chromatography on a Biotage cartridge with methylene chloride and acetone as solvents. Two fractions were further purified by HPLC using a Phenomenex column with water and acetonitrile as solvents resulting in the pure taccalonolides AP and AQ in fractions 27 and 32 respectively. AR was purified by HPLC using fractions 90-91 from the initial flash purification and was found in the HPLC fraction 26.

Hydrolysis of the Taccalonolides A, E and Z to Yield Taccalonolides B, N, and AB Respectively.

Taccalonolide A (40 mg) was dissolved in 4 mL of methanol and to this solution 8 mL of 0.05 M sodium bicarbonate was added. The solution was stirred at room temperature for 44 hours. The reaction solution was extracted with EtOAc and purified on HPLC to yield 25.8 mg of taccalonolide B. Taccalonolides N and AB were produced by hydrolysis of taccalonolides E and Z, respectively, using the same method. Taccalonolide AB was obtained as white powder. The LC/MS showed pseudomolecular ions at 677 $[M+H]^+$, 694 $[M+NH_4]^+$, and 699 $[M+Na]^+$, indicating the loss of an acetyl group from taccalonolide Z. The proton NMR showed the chemical shift of H-15 of taccalonolide AB at δ 4.75 (ddd, J=3.5, 9.0, 11.6 Hz), which is shifted 0.78 ppm up-field than that of taccalonolide Z, suggesting the loss of acetyl group at 15-OH. The HMBC correlation between 15-OH (δ 4.94) and C-15 (δ 71.5) confirmed the assignment.

Taccalonolide AB:

white powder; ESIMS: 677 [M+H]+, 694 [M+NH4]+, and 699 [M+Na]+. $^1$H NMR: δ (ppm) 5.27 (dd, J=11.9, 2.1 Hz, H-11), 5.22 (d, J=2.1 Hz, H-12), 5.01 (br., H-21), 4.93 (d, J=3.6 Hz, 15-OH), 4.91 (dd, J=10.8, 4.6 Hz, H-7), 4.83 (d, J=5.4 Hz, H-1), 4.62 (br, 25-OH), 4.47 (ddd, J=11.1, 9.0, 3.4 Hz, H-15), 4.05 (d, J=4.5 Hz, 7-OH), 3.76 (t, J=4.5 Hz, H-2), 3.69 (s, 5-OH), 3.63 (m, H-3), 3.17 (t, J=11.6 Hz, H-9), 2.56 (brd, J=15.7 Hz, H-4a), 2.43 (dd, J=13.0, 11.0 Hz, H-16), 2.26 (m, J=16.8 Hz, H-4b), 2.24 (m, H-14), 2.17 (s, 3H, 1-OAc), 2.15 (m, H-20), 2.14 (s, 3H, 12-OAc), 1.99 (s, 3H, 11-OAc), 1.86 (dd, J=13.2, 9.9 Hz, H-17), 1.69 (s, 3H, H-27), 1.64 (q, J=10.9 Hz, H-8), 1.37 (s, 3H, H-28), 0.97 (s, 3H, H-18), 0.89 (d, 3H, J=7.0 Hz, H-21), 0.78 (s, 3H, H-19); $^{13}$C NMR: δ (ppm) 207.23 (C-6), 175.35 (C-26), 171.12 (12-OAc), 169.64 (1-OAc), 169.51 (12-OAc), 154.90 (C-22), 110.43 (C-21), 79.10 (C-25), 78.75 (C-5), 74.41 (C-12), 74.12 (C-1), 72.04 (C-7), 71.46 (C-15), 70.89 (C-11), 57.57 (C-14), 54.12 (C-3), 51.04 (C-24), 50.79 (C-2), 50.28 (C-16), 48.19 (C-17), 46.06 (C-10), 44.06 (C-14), 43.82 (C-8), 36.66 (C-9), 31.17 (C-20), 27.07 (C-4), 25.62 (C-28), 21.99 (C-27), 21.35 (12-OAc), 21.14 (11-OAc), 20.83 (1-OAc), 20.30 (C-21), 14.70 (C-19), 13.44 (C-18).

Hydrolysis of Taccalonolide N Fraction and Isolation of Taccalonolides AK, AL, AM and AN.

The taccalonolide E fraction from the roots and rhizomes of *Tacca chantrieri* was hydrolyzed with mild base hydrolysis to produce predominantly taccalonolide N. This taccalonolide N enriched sample was further purified by HPLC using a C18 Phenomenex column and a solvent mixture of water and acetonitrile. Taccalonolide AN was found in fraction 9, taccalonolide AK in fraction 10, taccalonolide AL in fraction 24 and taccalonolide AM in fraction 22.

Hydrogenation of Taccalonolide A.

6 mg of taccalonolide A was dissolved in MeOH and 0.5 mg of Pd—C was added. A stream of $H_2$ was bubbled into the solution using a balloon. The reaction was kept at room temperature for 6 h. The solution was filtered and dried to obtain dihydrotaccalonolide A.

Reduction of Taccalonolide A.

6 mg of taccalonolide A was dissolved in 1 mL of MeOH and the solution was cooled on ice. $NaBH_4$ (3 mg) was added and stirred for 10 min. The solution was dried using miVac and the residue was extracted with $CH_2Cl_2$. The extract was dried and separated by HPLC to yield TA-$NaBH_4$-10 and TA-$NaBH_4$-12.

Acetylation of Taccalonolide B.

Taccalonolide B (3 mg) was dissolved in 0.3 mL of acetic anhydride. To this solution, 0.3 mL of anhydrous pyridine was added and was kept at room temperature for 48 h. The reaction solution was dried in miVac and separated using C18 HPLC to yield taccalonolide A and TB-Ac-16.

Epoxidation of the Taccalonolides.

Taccalonolide A (3.5 mg) was dissolved in 0.5 mL of methylene chloride and cooled to −20° C. with an ice salt bath. Dimethyldioxirane (0.1M, 75 μL) was added to the above solution. The temperature of the reaction was allowed to increase to room temperature and kept there until the reaction completed (approximately 4 h). The solvent was removed under vacuum and pure taccalonolide AF was obtained as white powder with 100% yield. The other epoxytaccalonolides were prepared using the same method. Taccalonolide AJ was produced using the above reaction with taccalonolide B as the starting material. This method is also applicable to epoxidate the crude taccalonolide extraction/fraction of *Tacca* spp. to produce the crude epoxytaccalonolide mixtures.

Taccalonolide AJ was isolated as a white powder. The ESI-MS showed a protonated molecular ion at m/z 677.2 $[M+H]^+$, which is one oxygen more than taccalonolide B. The proton NMR spectrum showed that H-22 was shifted from 5.00 ppm in taccalonolide B to 3.26 ppm, suggesting an epoxy group at C-22,23. No splitting of this signal requires the equatorial orientation of H-22, thus the epoxy group is a oriented. (FIG. 1).

Taccalonolide AJ:

white powder; ESIMS: m/z 677.2 $[M+H]^+$, 694.2 $[M+NH_4]^+$, 699.2 $[M+Na]^+$, 649.2 $[M-H_2O+H]^+$, 631.3, 589.2, 571.3, 539.3, 529.2, 511.2, 479.2, 469.3; $^1$H NMR (500 MHz, $CDCl_3$) δ 5.32 (dd, J=11.6, 2.5 Hz, H-11), 5.24 (d, J=3.1 Hz, H-12), 5.18 (d, J=2.4 Hz, 15-OH), 5.04 (s, 25-OH), 4.68 (d, J=5.5 Hz, H-1), 4.52 (br, 7-OH), 4.35 (dd, J=5.3 Hz, H-15), 4.17 (d, J=10.8 Hz, H-7), 3.50 (dd, J=4.5 Hz, H-2), 3.41 (br, H-3), 3.26 (s, H-22), 2.80 (dd, J=11.3, 4.3 Hz, H-5), 2.70 (t, J=11.5 Hz, H-9), 2.30-2.1 (m, H-4,14,16,17), 2.17 (s, 1-OAc), 2.14 (s, 12-OAc), 1.99 (S, 11-OAc), 1.36 (s, 3H), 1.76 (s, H-27), 1.36 (s, H-28), 1.02 (d, J=7.9 Hz, H-21), 0.85 (s, H-18), 0.84 (s, H-18).

Cell Culture.

The HeLa cervical cancer cell line, the SK-OV-3 ovarian cancer cell line and the PC-3 prostate cancer cell line were obtained from American Type Tissue Culture Collection (Manassas, Va.) and grown in Basal Media Eagle (BME) or RPMI 1640 medium (Invitrogen; Carlsbad, Calif.) supplemented with 10% fetal bovine serum (Hyclone; Logan, Utah) and 50 μg/ml gentamicin sulfate (Invitrogen). The P-glycoprotein expressing SK-OV-3/MDR-1-6/6 cell line and the βIII-tubulin expressing WTβIII cell line have been described previously (Risinger et al., 2008).

Inhibition of Cellular Proliferation and Initiation of Cytotoxicity.

The antiproliferative and cytotoxic effects of the taccalonolides were evaluated using the SRB assay (Skehan et al., 1990, Boyd and Paull, 1995) as previously described (Tinley et al., 2003). The concentration of drug that causes 50% inhibition of cellular proliferation ($IC_{50}$) was calculated from the linear portion of the log dose response curve. The ability of the compounds to initiate cytotoxicity was also determined Paclitaxel was included as a reference compound. The determination of $IC_{50}$ values was performed on taccalonolide material after NMR analysis and subsequent lyophilization. Ethanol or DMSO was used as the vehicle for all cellular studies.

Immunofluorescence.

Cellular microtubules in interphase and mitotic HeLa cells were visualized using indirect immunofluorescence techniques as previously described (Tinley et al., 2003). Cells were treated for 18 h with vehicle, the taccalonolides or the positive control paclitaxel, fixed with methanol and microtubules visualized with a β-tubulin antibody. Representative images of interphase and mitotic cells were acquired using a Nikon Eclipse 80i fluorescence microscope and compiled using NIS Elements AR 3.0 software.

Flow Cytometry.

HeLa cells were incubated for 18 h with vehicle, each taccalonolide or paclitaxel as a positive control. The cells were harvested and the DNA was stained with propidium iodide using Krishan's reagent (Krishan, 1975). Cellular DNA content was analyzed using a FACS Calibur flow cytometer (BD Biosciences). Data were plotted as propidium iodide intensity versus the number of events using ModFit LT 3.0 software (Verity Software, Topsham, Me.).

Microtubule Stabilization and Mitotic Arrest.

The ability of the newly isolated taccalonolides to cause bundling of interphase microtubules was evaluated in HeLa cells. Consistent with the effects of taccalonolides A and E, which were shown to exert interphase microtubule bundling in previous studies (Tinley et al., 2003), taccalonolides AF, AI, and AJ each caused the formation of thick bundled microtubule tufts typical of microtubule stabilizers including paclitaxel (FIG. 2A-D). Although microtubule stabilizers cause an increase in the density of interphase microtubules, the mechanism by which these agents inhibit the proliferation of cancer cells in vitro is widely accepted to be due to their ability to interrupt microtubule dynamics in mitosis, leading to mitotic arrest. The effect of the taccalonolides on mitotic progression was analyzed by flow cytometry. All taccalonolides caused an accumulation of cells in the $G_2/M$ phase of the cell cycle with 4N DNA content (FIG. 3A-D). This accumulation is identical to the mitotic arrest that is observed after treatment of HeLa cells with paclitaxel (FIG. 3A-D). Recent data also suggests that the ability of microtubule stabilizers to interrupt cellular trafficking and metabolism in interphase cells also leads to the initiation of cell death (Reviewed in Komlodi-Pasztor, 2011).

The effects of the taccalonolides on mitotic spindle structures were evaluated to test whether they caused mitotic spindle defects leading to cell cycle arrest. β-tubulin and DNA were visualized in HeLa cells by indirect immunofluorescence and DAPI staining, respectively. The majority of cells treated with each taccalonolide at the concentration that caused $G_2/M$ accumulation were found to be in mitosis as evidenced by a "rounded up" cellular morphology and condensed DNA. These mitotic cells contained multiple abnormal mitotic spindles, which is another common effect of microtubule stabilizing agents (FIGS. 4A-D). These findings demonstrate that all taccalonolides, including AF, AI and AJ are microtubule stabilizers that cause mitotic arrest of cells with multiple abnormal mitotic spindles.

Antiproliferative Activities of the Taccalonolides.

The antiproliferative potencies of the taccalonolides were evaluated in HeLa cells using the SRB assay. Several new taccalonolides with low nanomoloar potency were identified, Table 1. The most potent taccalonolide is the newly synthesized taccalonolide AI-epo, with an $IC_{50}$ value of 0.73 nM (Table 1). This makes taccalonolide AI-epo the most potent taccalonolide identified thus far. Each of the taccalonolides tested also initiates cytotoxicity. This low nanomolar potency of some of the new taccalonolides is identical or superior to other naturally occurring microtubule stabilizers, including paclitaxel, the epothilones, laulimalide and peloruside A, in comparison to the taccalonolides A and E (Risinger et al., 2008).

Tubulin Binding Activity of the Taccalonolides.

Figure 5:
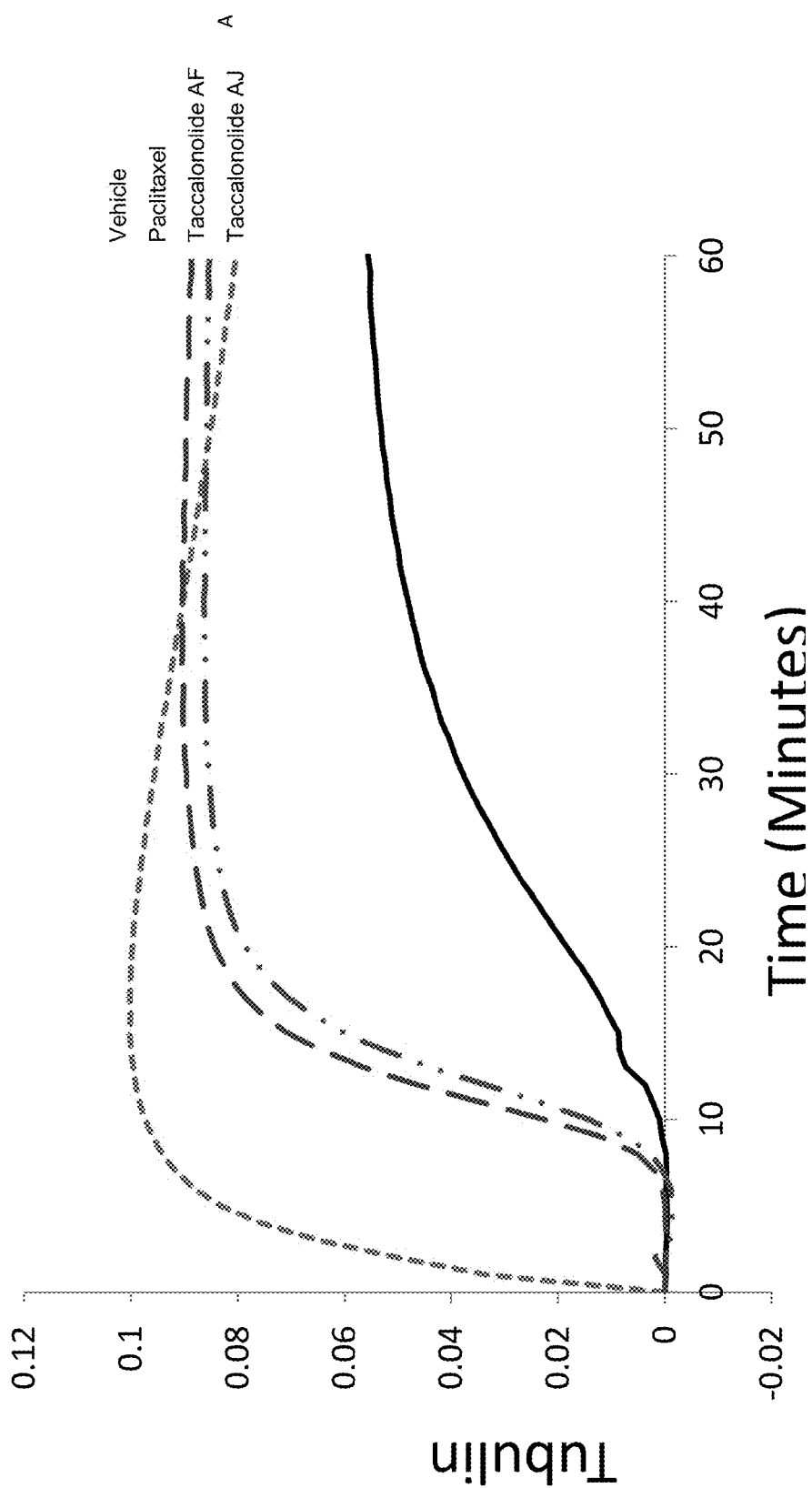
FIG. 5—Effect of the taccalonolides on purified porcine brain tubulin. 2 mg/ml porcine brain tubulin in 10% glycerol and 1 mM GTP was incubated at 37° C. in the presence of vehicle or 10 μM paclitaxel, taccalonolide AF or taccalonolide AJ. Tubulin polymerization was monitored by turbidity measurement at $OD_{340}$.

The ability of these new potent taccalonolides to interact directly with tubulin was assessed by incubating purified porcine brain tubulin at a concentration of 2 mg/ml in the presence of 10% glycerol and 1 mM GTP, which allows for a baseline level of tubulin polymerization that can be followed turbidimetrically (FIG. 5). The rate and extent of tubulin polymerization is dramatically increased when 10 μM of taccalonolide AF or AJ is added to the tubulin polymerization reaction, which is similar to the effects of the known microtubule interacting drug paclitaxel in this assay (FIG. 5). This result indicates that these potent taccalonolides can interact with purified tubulin and/or microtubules to enhance their polymerization.

Antitumor Activity of Taccalonolide AF.

Figure 6:
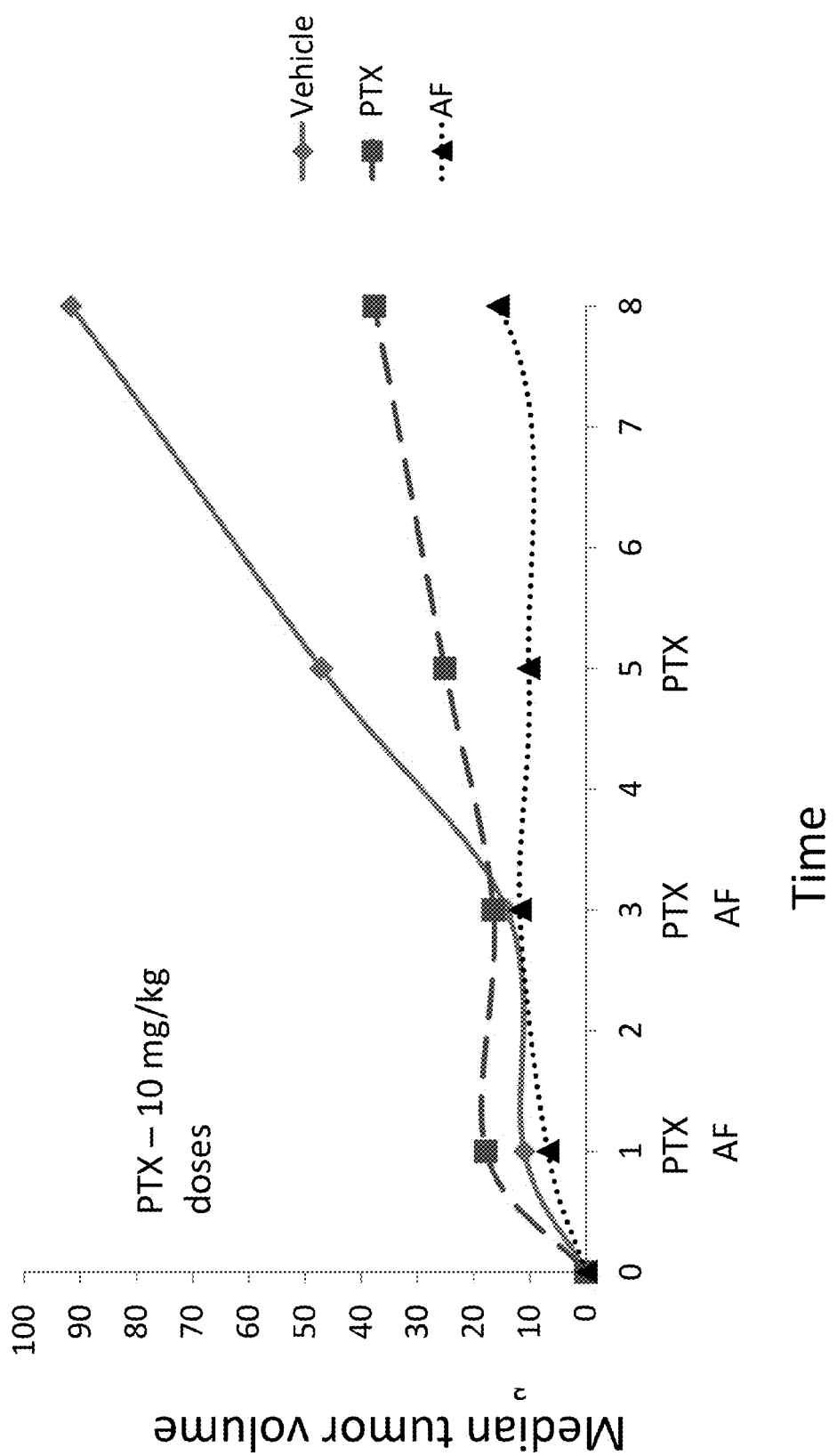
FIG. 6—Antitumor activity of taccalonolide AF. Nude mice bearing bilateral MDA-MB-231 human breast tumors were treated with vehicle, 10 mg/kg paclitaxel on days 1, 3 and 5 or 2.5 mg/kg taccalonolide AF on days 1 and 3. Tumor size was measured using calipers and volume calculated with the formula: Tumor volume (mm$^3$)=width (mm)×length (mm)×height (mm) and graphed as median tumor size for days 0-8.

The ability of taccalonolide AF to inhibit the growth of the aggressive human breast tumor MDA-MB-231 in a murine host was determined Taccalonolide AF was administered at a dose of 2.5 mg/kg on days 1 and 3. This dose of taccalonolide AF was sufficient to observe antitumor activity compared to vehicle treated controls (FIG. 6). This dose and schedule of AF also had greater antitumor activity than the positive control of 10 mg/kg paclitaxel administered on days 1, 3 and 5 over the first week of treatment (FIG. 6). This preliminary result demonstrates that taccalonolide AF has antitumor activity.

Efficacy of the Taccalonolides in Drug Resistant and Sensitive Cell Lines.

The ability of taccalonolides AF and AJ to inhibit the proliferation of both drug sensitive cancer cells, including ovarian cancer cells (SK-OV-3), cervical cancer cells (HeLa) and prostate cancer cells (PC-3) and drug resistant cells, including the P-glycoprotein expressing SK-OV-3 line (SK-OV-3/MDR-1-6/6) and the βIII-tubulin expressing HeLa cell line (WTβIII) was determined $IC_{50}$ values were calculated for each cell line and the relative resistance of these cell lines to AF, AJ and paclitaxel (a drug that is susceptible to both modes of resistance) were determined by dividing the $IC_{50}$ of the drug resistant cell line by the $IC_{50}$ of the parental line. The relative resistance of taccalonolides AF and AJ in both cell line pairs was much lower than paclitaxel (FIG. 7), indicating that, like previously identified taccalonolides, the potent taccalonolides AF and AJ are able to circumvent clinically relevant drug resistance associated with either overexpression of P-glycoprotein or βIII-tubulin. Additionally, the ability of the taccalonolides AF and AJ to potently inhibit the proliferation of a variety of cancer cell lines, including ovarian, cervical and prostate lines, suggests they may have a broad efficacy against many types of cancer.

Taccalonolides AF and AJ are not Cytotoxic to Normal Cells.

The taccalonolides AF and AJ were added to human mammary epithelial cells at concentrations 5 to 100-fold their I $IC_{50}$ values in the HeLa cancer cell line. No cytotoxicity of these normal cells was observed at any of the concentrations tested, indicating that these new potent taccalonolides do not kill normal epithelial cells at concentrations two orders of magnitude greater than the concentration that causes significant antiproliferative effects in cancer cells.

Structure-Activity of the Taccalonolides.

Preliminary SAR of the taccalonolides has been described (Li et al., 2011, Peng et al., 2010, Risinger et al., 2008). Taccalonolide AF, which differs from taccalonolide A only by conversion of the C22-C23 double bond to an epoxide group, has an $IC_{50}$ value of 23 nM (Table 1), which is a 234-fold increase in potency as compared of taccalonolide A. The conversion of taccalonolide B to taccalonolide AJ by epoxidation at this same site resulted in a 743-fold increase in potency. The importance of the C22-C23 epoxide moeity to biological potency led to the epoxidation of 23 additional taccalonolides. Each of the taccalonolides with an epoxide group at C22-C23 was significantly more potent than the parent taccalonolide (Table 1). AI-epo, the epoxide product of taccalonolide AI, was the most potent taccalonolide generated with an $IC_{50}$ of 0.73 nM. These results indicate that an epoxide moiety at C22-C23 has a major impact on biological potency. Taccalonolide AC, which differs with taccalonolide A by an additional hydroperoxyl group at C20, showed no activity at concentrations as high as 50,000 nM. Taccalonolides AK and AO, both of which contain a six-member lactone ring and C23 carbonyl groups in place of the five-member lactone ring of other taccalonolides, showed no activity at concentrations as high as 30,000 nM. Taken together, these results highlight the importance of the C20-C22-C23 region of the taccalonolide molecule and suggest that this region plays a central role in its interaction with tubulin/microtubules.

The taccalonolides S, T, AG, AH, AI and AM, which all contain isobutyrate or isopentyrate groups at C1, are more potent than the taccalonolides E, R, AP, N and AL, which have an acyloxy group at C1. These results suggest that a bulky substituent at C1 is optimal for biological potency. Taccalonolides AQ, AR and AS, in which the C2-C3 epoxide ring has been opened and replaced with a chlorine group, showed little to no activity at concentrations as high as 30,000 nM, suggesting this epoxide is also critical for optimal potency. When an OH group was introduced at C5 to taccalonolides E, N and AI which lack a C11 acyloxy to form taccalonolides AP, AL and AM, respectively, a decrease in potency was observed.

Introducing an OH group at C5 in taccalonolides A and B, which have an acyloxy group at C11, to form taccalonolides Z and AB resulted in increased potency. These results indicate the importance of the 5-OH group for potency is related to the presence or absence of the 11-acyloxy moiety. Acetylation of the OH moeity at C11 also increased activity, which was evidenced by comparing taccalonolides AA and R with taccalonolides Z and AP (Table 1). The less potent taccalonolides E, N, R, AP and AL, which lack an 11-acyloxy group as compared to the more potent taccalonolides A, B, AA, Z and AB, further demonstrates that an 11-acyloxy group is optimal for taccalonolide potency.

Hydrolysis of the C15 acetate in taccalonolides A, E, AF, AH and AP, to the resulting taccalonolides B, N, AJ, AI and AL, resulted in more potent taccalonolides. Taccalonolide Z is an exception to this finding since hydrolysis of the C15 group, yielded taccalonolide AB, which was significantly less potent. Taccalonolide H2 is 7.4-fold more potent than taccalonolide A and differs only by the presence of an additional double bond in taccalonolide H2 at C7-C8. The location of this double bond is important, since a double bond at C5-C6 (as is found in taccalonolide AD) did not result in increased potency. When a hydroxyl group was added to the C7 of taccalonolide A to form the rare geminal diol in taccalonolide AE, the potency was also unchanged.

The microtubule stabilizing activity of each taccalonolide correlates with its antiproliferative and cytotoxic potency, demonstrating that these properties of the taccalonolides are directly related to one another.

TABLE 1

Antiproliferative Potency of Taccalonolides Compared with their Corresponding Epoxides.

| Taccalonolide | $IC_{50}$ (nM) | Corresponding Epoxide | $IC_{50}$ (nM) |
| --- | --- | --- | --- |
| Taccalonolide A | 5,380 | Taccalonolide AF | 23 |
| Taccalonolide B | 3,120 | Taccalonolide AJ | 4.3 |
| Taccalonolide E | 39,500 | TE-epo | 67 |
| Taccalonolide I | >10,000 | I-epo | 327 |
| Taccalonolide N | 8,500 | TN-epo | 11 |
| Taccalonolide R | 13,144 | TR-epo | 18 |
| Taccalonolide S | 9 | N/A | |
| Taccalonolide T | 335 | N/A | |
| Taccalonolide H2 | 730 | H2-epo | 37 |
| Taccalonolide Z | 120 | Z-epo | 21 |
| Taccalonolide AA | 32.3 | AA-epo | 15 |
| Taccalonolide AB | 2,767 | AB-epo | 5.0 |
| Taccalonolide AC | >50,000 | AC-epo | ~40 μM |
| Taccalonolide AD | 3,480 | AD-epo | 338 |
| Taccalonolide AE | 5,010 | AE-epo | 422 |
| Taccalonolide AG (in mixture with AH) | 32 | | |
| Taccalonolide AH | 158 | AH-epo | 7 |
| Taccalonolide AI | 47 | AI-epo | 0.73 |
| Taccalonolide AK | >30,000 | N/A | |
| Taccalonolide AL | 18,000 | AL-epo | 134 |
| Taccalonolide AM | 1,200 | AM-epo | 16 |
| Taccalonolide AN | 1,000 | AN-epo | 265 |
| Taccalonolide AO | >30,000 | NA | |
| Taccalonolide AP | >30,000 | AP-epo | 333 |
| Taccalonolide AQ | >30,000 | AQ-epo | 463 |
| Taccalonolide AR | >30,000 | AR-epo | 366 |
| Taccalonolide AS | >10,000 | AS-epo | ~25 μM |
| TA-NaBH4-12 | 7,500 | TA-NaBH4-12-epo | 131 |
| TA-NaBH4-10 | 20,000 | TA-NaBH4-10-epo | 235 |
| TB-AC-16 | 40,000 | TB-Ac-16-epo | 252 |

The concentrations of drugs that caused a 50% inhibition of cellular proliferation ($IC_{50}$) were measured in HeLa cells using the SRB assay.
N/A is not available.

TABLE 2
Chemical Formulas of Taccalonolide Comparison Compounds.
| Compound Name | Structure |
| --- | --- |
| Taccalonolide A | 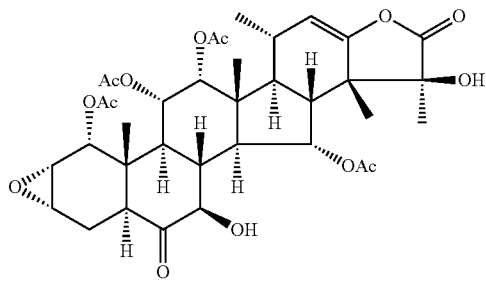 |
| Taccalonolide B | 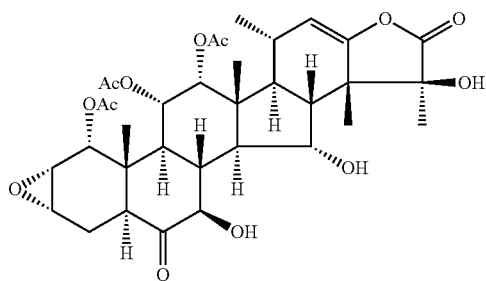 |
| Taccalonolide C | 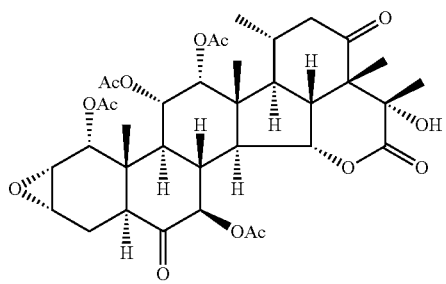 |
| Taccalonolide D | 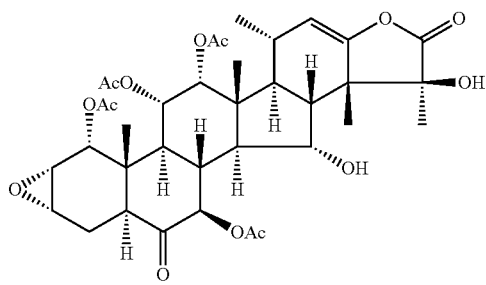 |
| Taccalonolide E | 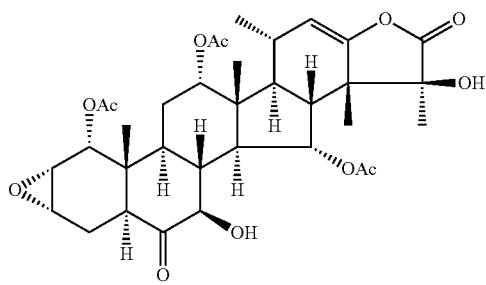 |

TABLE 2-continued
Chemical Formulas of Taccalonolide Comparison Compounds.
Compound Name | Structure
Taccalonolide F
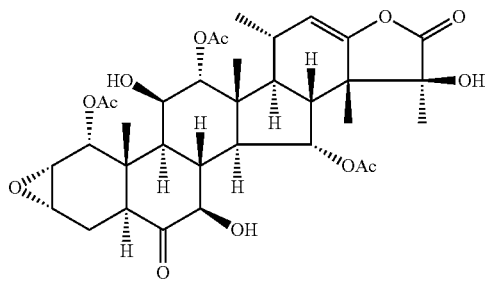
Taccalonolide G
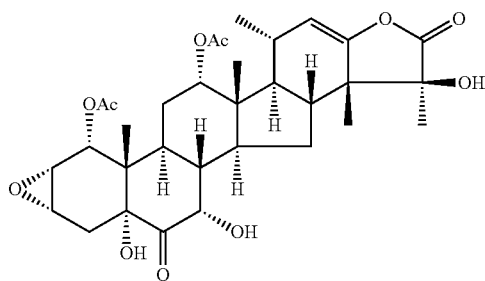
Taccalonolide H
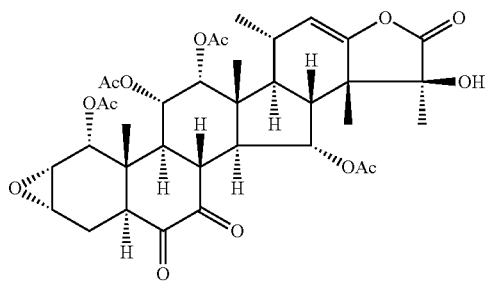
Taccalonolide I
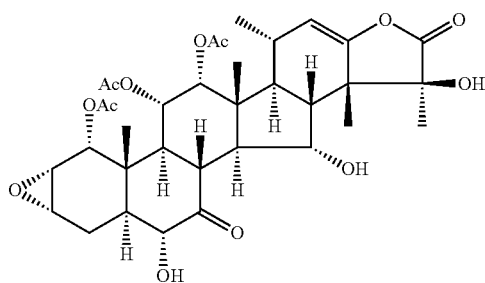
Taccalonolide J
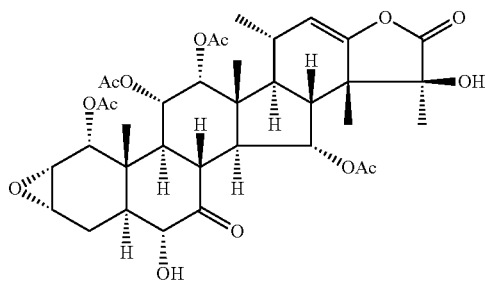

TABLE 2-continued
Chemical Formulas of Taccalonolide Comparison Compounds.
| Compound Name | Structure |
|---|---|
| Taccalonolide K | 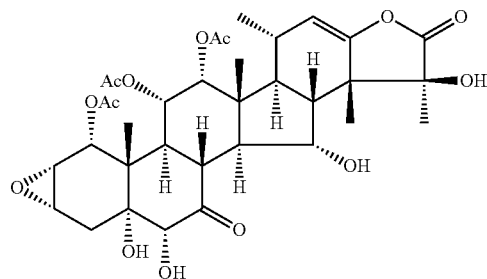 |
| Taccalonolide L | 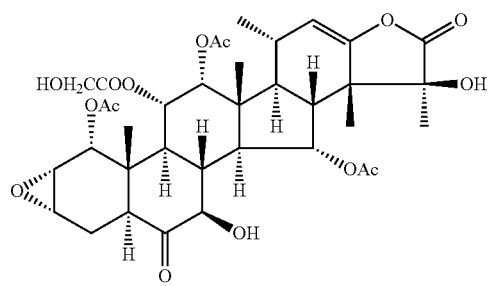 |
| Taccalonolide M | 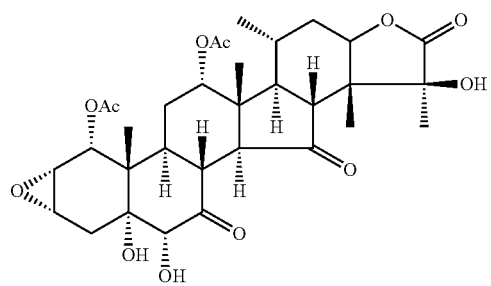 |
| Taccalonolide N | 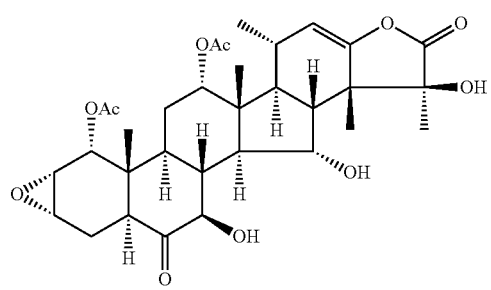 |
| Taccalonolide O | 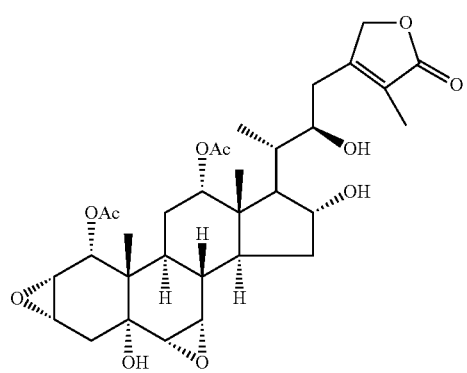 |

TABLE 2-continued

Chemical Formulas of Taccalonolide Comparison Compounds.

| Compound Name | Structure |
|---|---|
| Taccalonolide P | 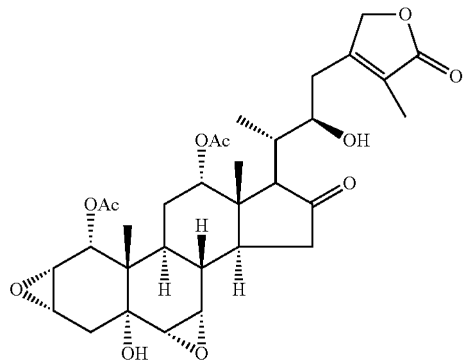 |
| Taccalonolide Q | 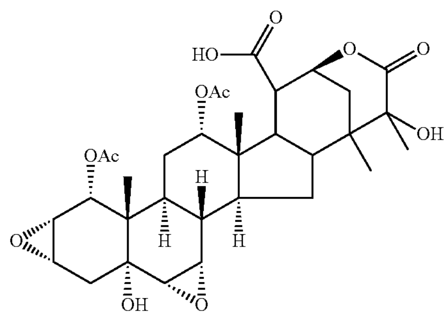 |
| Taccalonolide R | 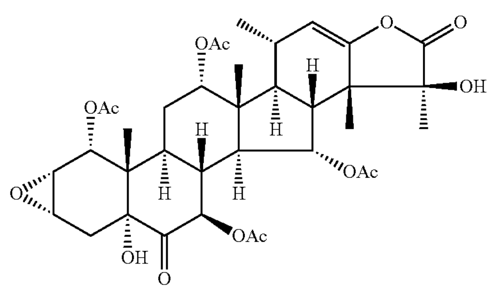 |
| Taccalonolide S | 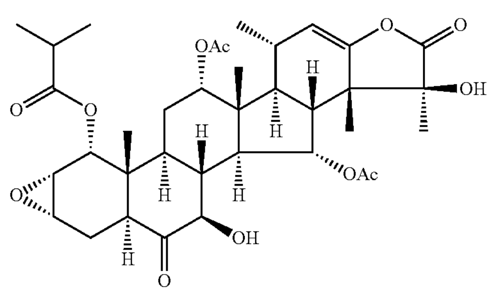 |
| Taccalonolide T | 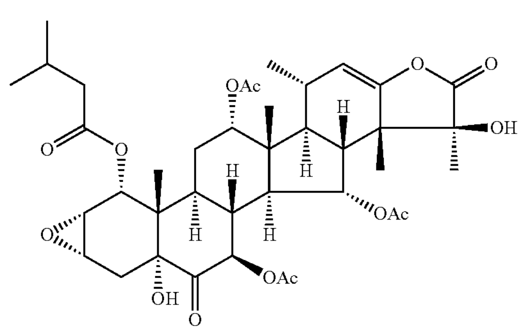 |

TABLE 2-continued
Chemical Formulas of Taccalonolide Comparison Compounds.
| Compound Name | Structure |
| --- | --- |
Taccalonolide U
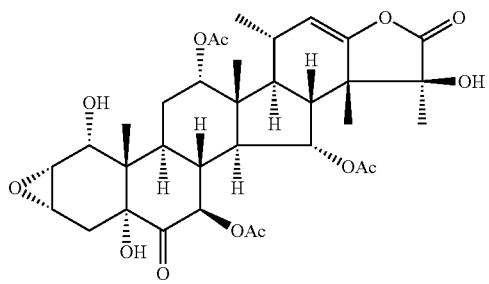
Taccalonolide V
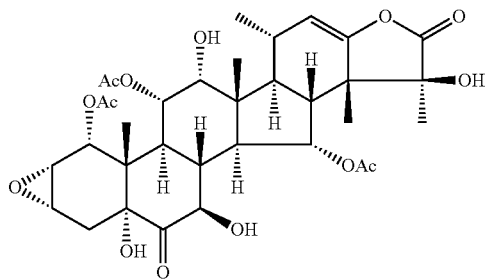
Taccalonolide W
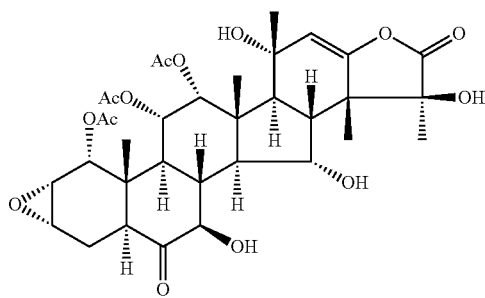
Taccalonolide X
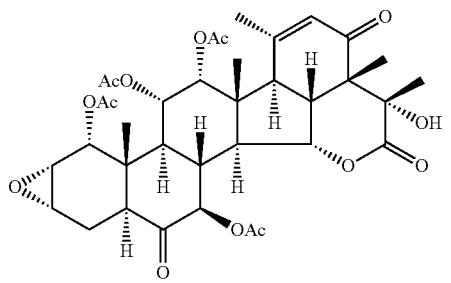
Taccalonolide Y
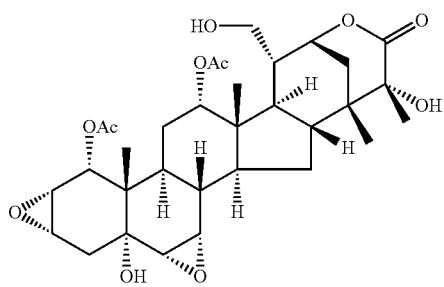

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substituents and modifications apparent to those skilled in the art are deemed to be within the spirit, scope and concept of the invention as defined by the appended claims.

IV. REFERENCES

The following references, to the extent that they provide exemplary procedural or other details supplementary to those set forth herein, are specifically incorporated herein by reference:

Bennett et al., *Chem. Biol.*, 17:725-734, 2010.
Boyd and Paull, *Drug Develop. Res.* 34:91-109, 1995.
Chen et al., *Phytochem.*, 27:2999-3002, 1988.
Chen et al., *Planta Medica*, 63:40-43, 1997.
Chen et al., *Tetrahedron Ltrs.*, 28:1673-1676, 1987.
Corbett et al., *Cancer Treat. Rep.*, 62:1471-88, 1978.
Fojo and Menefee, *Annual Oncol.*, 18(5):v3-8, 2007.
Galsky et al., *Nat. Rev. Drug Discov.*, 9(9):677-678, 2010.
Handbook of Pharmaceutical Salts: Properties, and Use (P. H. Stahl & C. G. Wermuth eds.), Verlag Helvetica Chimica Acta, 2002.
Huang and Liu, *Helvetica Chimica Acta*, 85:2553-2558, 2002.
Komlodi-Pasztor et al., *Nat Rev Clin Oncol*, 8:244-250, 2011.
Krishan, *J. Cell Biol.*, 66:188-193, 1975.
Li et al., *J. Am. Chem. Soc.*, 133:19064-19067, 2011.
Morris and Fornier, *Clin. Cancer Res.*, 14(22):7167-7172.
Muhlbauer and Seip, *Helvetica Chimica Acta*, 86:2065-2072, 2003.
Nogales et al., *Nature*, 375:424-427, 1995.
Peng et al., *J Med Chem Epub Aug.* 11, 2011.
PCT Publn. WO/2001/040256
Polin et al., In: *Transplantable Syngeneic Rodent Tumors: Solid Tumors of Mice*, 2nd Ed., Humana Press Inc., Totowa, N.J., 43-78, 2011.
Remington's Pharmaceutical Sciences, 15th Ed., 1035-1038 and 1570-1580, 1990.
Remington's Pharmaceutical Sciences, 15th Ed., 3:624-652, 1990.
Risinger et al., *Cancer Res.*, 68:8881-8888, 2008.
Shen et al., *Chinese J. Chem.*, 9:92-94, 1991.
Shen et al., *Phytochem.*, 42:891-893, 1996.
Shen et al., *J. Pharmacol. Exp. Ther.* 337:423-432, 2011.
Skehan et al., *J. Natl. Cancer Inst.*, 82:1107-1112, 1990.
Tinley et al., *Cancer Res.*, 63:3211-3220, 2003.
Yang et al., *Helvetica Chimica Acta*, 91:1077-1082, 2008.

The invention claimed is:

1. A compound of the formula:

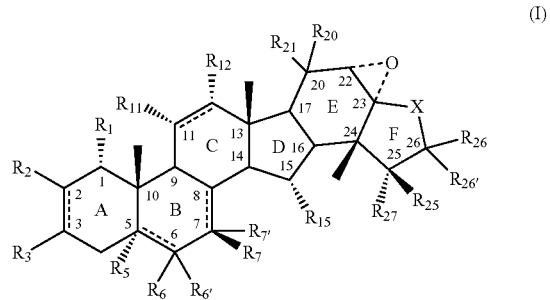

wherein:

$R_1$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_2$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof, or $R_2$ is taken together with $R_3$ to form an epoxide at C-2/C-3;

$R_3$ is hydrogen, amino, cyano, azido, halo, hydroxy, oxo, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, and substituted versions thereof, or $R_3$ is taken together with $R_2$ as defined above;

$R_5$ is absent, hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_6$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof, or oxo if $R_{6'}$ is not present, or $R_6$ is taken together with $R_7$ to form an epoxide at C-6/C-7;

$R_{6'}$ when present is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof;

$R_7$ is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C \leq 12)}$, amido$_{(C \leq 12)}$, alkylthio$_{(C \leq 12)}$, aryl$_{(C \leq 12)}$, aralkyl$_{(C \leq 12)}$, heterocycloalkyl$_{(C \leq 12)}$, or substituted versions thereof, or oxo if $R_{7'}$ is not present, or $R_7$ is taken together with $R_6$ as defined above;

$R_{7'}$ when present is hydrogen, amino, cyano, azido, halo, hydroxy, alkyl$_{(C \leq 12)}$, alkenyl$_{(C \leq 12)}$, alkoxy$_{(C \leq 12)}$, acyl$_{(C \leq 12)}$, acyloxy$_{(C \leq 12)}$, alkylamino$_{(C \leq 12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{11}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{12}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{15}$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{20}$ is hydrogen, amino, cyano, azido, halo, hydroxy, hydroperoxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{21}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{25}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{26}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if $R_{26'}$ is not present;

$R_{26'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{27}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof; and X is O, NR' or CR'$_2$, wherein each R' is independently hydrogen or alkyl$_{(C\leq6)}$;

or a pharmaceutically acceptable salt thereof;

provided, however, that Formula I does not include the compound wherein $R_1$ is acetoxy, $R_2$ taken together with $R_3$ forms an epoxide at C-2/C-3; $R_5$ is hydrogen, $R_6$ is oxo and $R_{6'}$ is not present, $R_7$ is hydroxy and $R_{7'}$ is hydrogen, each of $R_{11}$, $R_{12}$ and $R_{15}$ are acetoxy, one of $R_{20}$ or $R_{21}$ is methyl and the other is hydrogen, $R_{25}$ is OH, $R_{26}$ is oxo and $R_{26'}$ is not present, $R_{27}$ is methyl, and X is O.

2. The compound of claim 1, wherein:

$R_1$ is hydroxy, alkoxy$_{(C\leq12)}$ or acyloxy$_{(C\leq12)}$;

$R_2$ is hydroxy, halogen, alkoxy$_{(C\leq12)}$ or acyloxy$_{(C\leq12)}$, or $R_2$ is taken together with $R_3$ to form an epoxide at C-2/C-3;

$R_3$ is hydroxy, halogen, alkoxy$_{(C\leq12)}$ or acyloxy$_{(C\leq12)}$, or $R_2$ is taken together with $R_3$ as defined above;

$R_5$ is hydrogen, hydroxy, amino, alkoxy$_{(C\leq9)}$, alkylamino$_{(C\leq6)}$, or dialkylamino$_{(C\leq12)}$;

$R_6$ is hydrogen, hydroxy, alkoxy$_{(C\leq8)}$, acyloxy$_{(C\leq8)}$, amide$_{(C\leq12)}$, alkylamino$_{(C\leq12)}$, dialkylamino$_{(C\leq12)}$, or oxo;

$R_{6'}$ when present is hydrogen, hydroxy, alkoxy$_{(C\leq8)}$, acyloxy$_{(C\leq8)}$, amide$_{(C\leq12)}$, alkylamino$_{(C\leq12)}$ or dialkylamino$_{(C\leq12)}$;

$R_7$ is hydrogen, hydroxy, alkoxy$_{(C\leq8)}$, acyloxy$_{(C\leq8)}$, or oxo if $R_{7'}$ is not present;

$R_{7'}$ when present is hydrogen, hydroxy, alkoxy$_{(C\leq8)}$, or acyloxy$_{(C\leq8)}$;

$R_{11}$ is hydrogen, hydroxy, alkoxy$_{(C\leq8)}$, or acyloxy$_{(C\leq8)}$;

$R_{12}$ is hydrogen, hydroxy, alkoxy$_{(C\leq8)}$, or acyloxy$_{(C\leq8)}$;

$R_{15}$ is hydrogen, hydroxy, alkoxy$_{(C\leq8)}$ or acyloxy$_{(C\leq8)}$;

$R_{20}$ is hydrogen, methyl, hydroxy, hydroperoxy, alkoxy$_{(C\leq8)}$ or acyloxy$_{(C\leq8)}$;

$R_{21}$ is hydrogen or methyl;

$R_{25}$ is hydrogen, hydroxy, alkoxy$_{(C\leq8)}$ or acyloxy$_{(C\leq8)}$;

$R_{26}$ is hydrogen, hydroxy, alkoxy$_{(C\leq8)}$ or oxo if $R_{26'}$ is not present;

$R_{26'}$ when present is hydrogen, hydroxy or alkoxy$_{(C\leq8)}$;

$R_{27}$ is hydrogen or alkyl$_{(C\leq6)}$; and

X is O, NR' or CR'$_2$, wherein each R' is independently hydrogen or alkyl$_{(C\leq6)}$;

or a pharmaceutically acceptable salt thereof.

3. The compound of claim 1, wherein $R_1$ is acyloxy$_{(C\leq12)}$, acetyloxy, isobutyrate, isovalerate, alkoxy, or hydroxy.

4. The compound of claim 1, wherein one or both of $R_2$ and/or $R_3$ are acyloxy$_{(C\leq12)}$, or $R_2$ and $R_3$, taken together, form an epoxide at C-2/C-3.

5. The compound of claim 1, wherein $R_5$ is hydrogen, hydroxy, alkoxy, acyloxy, or $R_5$ is absent.

6. The compound of claim 1, wherein $R_6$ is oxo, hydroxy, acyloxy$_{(C\leq12)}$, alkylamino$_{(C\leq12)}$ or dialkylamino$_{(C\leq12)}$, or $R_6$ and $R_7$, taken together, form an epoxide at C-6/C-7.

7. The compound of claim 1, wherein $R_7$ is acyloxy$_{(C\leq12)}$, acetyloxy, hydroxy, alkoxy or oxo.

8. The compound of claim 1, wherein $R_{15}$ is hydroxy, alkoxy, hydrogen, oxo, acyloxy$_{(C\leq12)}$, or acetyloxy.

9. The compound of claim 1, wherein X is O or NR'.

10. A compound having the structure:

wherein, unless otherwise indicated in the following table:
$R_2$ and $R_3$ taken together form an epoxide,
$R_6$ is oxo, and $R_{6'}$ is not present,
$R_{12}$ is —OAc,
$R_{20}$ is methyl,
$R_{21}$ is hydrogen,
$R_{25}$ is hydroxy,
$R_{26}$ is oxo, and $R_{26'}$ is not present,
$R_{27}$ is methyl,
X is O, and

| Compound | $R_1$ | $R_5$ | $R_7$ | $R_{7'}$ | $R_{11}$ | $R_{15}$ | Other |
|---|---|---|---|---|---|---|---|
| Taccalonolide AJ | —OAc | —H | —OH | —H | —OAc | —OH | |
| Epoxytaccalonolide V | —OAc | —OH | —OAc | —H | —OAc | —OAc | R12 = —OH |
| Epoxytaccalonolide H | —OAc | —H | =O | Abs. | —OAc | —OAc | |
| Epoxytaccalonolide AD | —OAc | Abs. | =O | Abs. | —OAc | —OAc | $R_6$ = —OH, $^{5,6}\Delta$ double bond |
| Epoxytaccalonolide AE | —OAc | —H | —OH | —OH | —OAc | —OAc | |
| Epoxytaccalonolide H2 | —OAc | —H | —OH | Abs. | —OAc | —OAc | $^{7,8}\Delta$ double bond |
| Epoxy-TA-NaBH4-12 | —OAc | —H | —OH | —H | —OAc | —OH | $R_6$ = —OAc, $R_{6'}$ = —H |
| Epoxy-TA-NaBH4-10 | —OAc | —H | —OH | —H | —OAc | —OH | $R_6$ = —OH, $R_{6'}$ = —H |
| Epoxy-TB-Ac-16 | —OAc | —H | —OAc | —H | —OAc | —OH | $R_{25}$ = —OAc |
| Epoxytaccalonolide D | —OAc | —H | —OAc | —H | —OAc | —OH | |
| Epoxytaccalonolide E | —OAc | —H | —OH | —H | —H | —OAc | |
| Epoxytaccalonolide F | —OAc | —H | —OH | —H | —OH | —OAc | |
| Epoxytaccalonolide L | —OAc | —H | —OH | —H | —OC(O)CH$_2$OH | —OAc | |
| Epoxytaccalonolide N | —OAc | —H | —OH | —H | —H | —OH | |
| Epoxytaccalonolide G | —OAc | —OH | —OH | —H | —H | —H | |
| Epoxytaccalonolide R | —OAc | —OH | —OAc | —H | —H | —OAc | |
| Epoxytaccalonolide S | isobutyrate | —H | —OH | —H | —H | —OAc | |
| Epoxytaccalonolide T | 3-methyl butanoate | —OH | —OAc | —H | —H | —OAc | |
| Epoxytaccalonolide U | —OH | —OH | —OAc | —H | —H | —OAc | |
| Epoxytaccalonolide Z | —OAc | —OH | —OH | —H | —OAc | —OAc | |
| Epoxytaccalonolide AA | —OAc | —OH | —OAc | —H | —OAc | —OAc | |
| Epoxytaccalonolide AB | —OAc | —OH | —OH | —H | —OAc | —OH | |
| Epoxytaccalonolide AG | 3-methyl butanoate | —OH | —OH | —H | —H | —OAc | |
| Epoxytaccalonolide AH | 3-methyl butanoate | —H | —OH | —H | —H | —OAc | |
| Epoxytaccalonolide AI | 3-methyl butanoate | —H | —OH | —H | —H | —OH | |
| Epoxytaccalonolide I | —OAc | —H | =O | Abs. | —OAc | —OH | $R_6$ = α-OH |
| Epoxytaccalonolide J | —OAc | —H | =O | Abs. | —OAc | —OAc | $R_6$ = α-OH |
| Epoxytaccalonolide K | —OAc | —OH | =O | Abs. | —OAc | —OH | $R_6$ = α-OH |
| Epoxytaccalonolide M | —OAc | —OH | =O | Abs. | —H | =O | $R_6$ = α-OH |
| Epoxytaccalonolide W | —OAc | —H | —OH | —H | —OAc | —OH | $R_{20}$ = OH, $R_{21}$ = Me |
| Epoxytaccalonolide AC | —OAc | —H | —OH | —H | —OAc | —OAc | $R_{20}$ = OOH, $R_{21}$ = Me |

11. A composition comprising at least 90% by weight of a compound of Formula I, wherein Formula I has the structure:

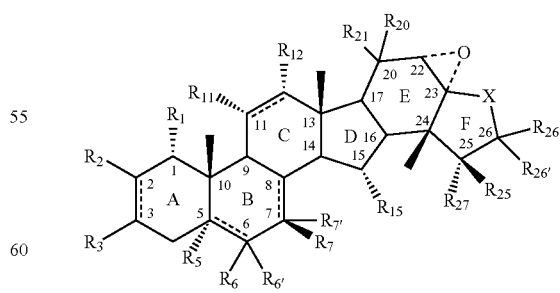

(I)

wherein:
$R_1$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_2$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or $R_2$ is taken together with $R_3$ to form an epoxide at C-2/C-3;

$R_3$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, and substituted versions thereof, or $R_3$ is taken together with $R_2$ as defined above;

$R_5$ is absent, hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_6$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if $R_{6'}$ is not present, or $R_6$ is taken together with $R_7$ to form an epoxide at C-6/C-7;

$R_{6'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_7$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if $R_{7'}$ is not present, or $R_7$ is taken together with $R_6$ as defined above;

$R_{7'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{11}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{12}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{15}$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{20}$ is hydrogen, amino, cyano, azido, halo, hydroxy, hydroperoxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{21}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{25}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{26}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof, or oxo if $R_{26'}$ is not present;

$R_{26'}$ when present is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_{27}$ is hydrogen, amino, cyano, azido, halo, hydroxy, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof; and X is O, NR' or CR'$_2$, wherein each R' is independently hydrogen or alkyl$_{(C\leq6)}$;

or a pharmaceutically acceptable salt thereof.

12. A composition comprising a compound of Formula I and a pharmaceutically acceptable carrier therefor, wherein Formula I has the structure:

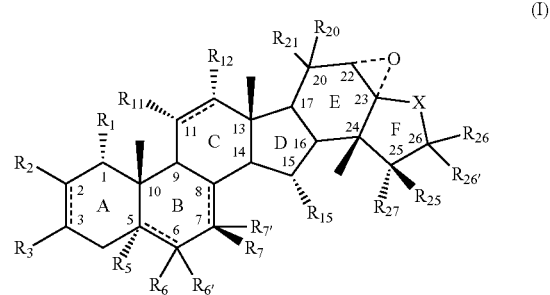

wherein:

$R_1$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C\leq12)}$, alkylthio$_{(C\leq12)}$, aryl$_{(C\leq12)}$, aralkyl$_{(C\leq12)}$, heterocycloalkyl$_{(C\leq12)}$, or substituted versions thereof;

$R_2$ is hydrogen, amino, cyano, azido, halo, hydroxy, oxo, alkyl$_{(C\leq12)}$, alkenyl$_{(C\leq12)}$, alkoxy$_{(C\leq12)}$, acyl$_{(C\leq12)}$, acyloxy$_{(C\leq12)}$, alkylamino$_{(C\leq12)}$, dialkylamino$_{(C\leq12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof, or R$_2$ is taken together with R$_3$ to form an epoxide at C-2/C-3;

R$_3$ is hydrogen, amino, cyano, azido, halo, hydroxy, oxo, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, and substituted versions thereof, or R$_3$ is taken together with R$_2$ as defined above;

R$_5$ is absent, hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_6$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof, or oxo if R$_{6'}$ is not present, or R$_6$ is taken together with R$_7$ to form an epoxide at C-6/C-7;

R$_{6'}$ when present is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_7$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof, or oxo if R$_{7'}$ is not present, or R$_7$ is taken together with R$_6$ as defined above;

R$_{7'}$ when present is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{11}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{12}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{15}$ is hydrogen, amino, cyano, azido, halo, hydroxy, oxo, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{20}$ is hydrogen, amino, cyano, azido, halo, hydroxy, hydroperoxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{21}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{25}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{26}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof, or oxo if R$_{26'}$ is not present;

R$_{26'}$ when present is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof;

R$_{27}$ is hydrogen, amino, cyano, azido, halo, hydroxy, alkyl$_{(C≤12)}$, alkenyl$_{(C≤12)}$, alkoxy$_{(C≤12)}$, acyl$_{(C≤12)}$, acyloxy$_{(C≤12)}$, alkylamino$_{(C≤12)}$, dialkylamino$_{(C≤12)}$, amido$_{(C≤12)}$, alkylthio$_{(C≤12)}$, aryl$_{(C≤12)}$, aralkyl$_{(C≤12)}$, heterocycloalkyl$_{(C≤12)}$, or substituted versions thereof; and X is O, NR' or CR'$_2$, wherein each R' is independently hydrogen or alkyl$_{(C≤6)}$;

or a pharmaceutically acceptable salt thereof.

13. The composition of claim 12, wherein, unless otherwise indicated in the following table, the compound is selected from the group consisting of compounds of Formula I wherein:

R$_2$ and R$_3$ taken together form an epoxide,
R$_6$ is oxo, and R$_{6'}$ is not present,
R$_{12}$ is —OAc,
R$_{20}$ is methyl,
R$_{21}$ is hydrogen,
R$_{25}$ is hydroxy,
R$_{26}$ is oxo, and R$_{26'}$ is not present,
R$_{27}$ is methyl,
X is O, and

| Compound | R$_1$ | R$_5$ | R$_7$ | R$_{7'}$ | R$_{11}$ | R$_{15}$ | Other |
|---|---|---|---|---|---|---|---|
| Taccalonolide AI | 3-methyl butanoate | —H | —OH | —H | —H | —OH | |
| Taccalonolide AA | —OAc | —OH | —OAc | —H | —OAc | —OAc | |
| Taccalonolide Z | —OAc | —OH | —OH | —H | —OAc | —OAc | |
| Taccalonolide AB | —OAc | —OH | —OH | —H | —OAc | —OH | |
| Taccalonolide AC | —OAc | —H | —OH | —H | —OAc | —OAc | R$_{20}$ = OOH, R$_{21}$ = Me |

-continued

| Compound | $R_1$ | $R_5$ | $R_7$ | $R_{7'}$ | $R_{11}$ | $R_{15}$ | Other |
|---|---|---|---|---|---|---|---|
| Taccalonolide AD | —OAc | Abs. | =O | Abs. | —OAc | —OAc | $R_6$ = OH, $^{5,6}\Delta$ double |
| Taccalonolide AE | —OAc | —H | —OH | —OH | —OAc | —OAc | |
| Taccalonolide AG | 3-methyl butanoate | —OH | —OH | —H | —H | —OAc | |
| Taccalonolide AH | 3-methyl butanoate | —H | —OH | —H | —H | —OAc | |
| Taccalonolide H2 | —OAc | —H | —OH | Abs. | —OAc | —OAc | $^{7,8}\Delta$ double bond |
| TA-NaBH4-12 | —OAc | —H | —OH | —H | —OAc | —OH | $R_6$ = —OAc, $R_{6'}$ = —H |
| TA-NaBH4-10 | —OAc | —H | —OH | —H | —OAc | —OH | $R_6$ = —OH, $R_{6'}$ = —H |
| TB-Ac-16 | —OAc | —H | —OAc | —H | —OAc | —OH | $R_{25'}$ = —OAc |
| Taccalonolide AL | —OAc | —OH | —OH | —H | —H | —OH | |
| Taccalonolide AM | 3-methyl butanoate | —OH | —OH | —H | —H | —OH | |
| Taccalonolide AN | —OH | —H | —OH | —H | —H | —OH | |
| Taccalonolide AP | —OAc | —OH | —OH | —H | —H | —OAc | |
| Taccalonolide AQ | —OH | —OH | —OH | —H | —OAc | —OAc | $R_2$ = —OAc $R_3$ = —Cl |

14. A composition comprising a compound and a pharmaceutically acceptable carrier therefor, wherein said compound is selected from the group consisting of:

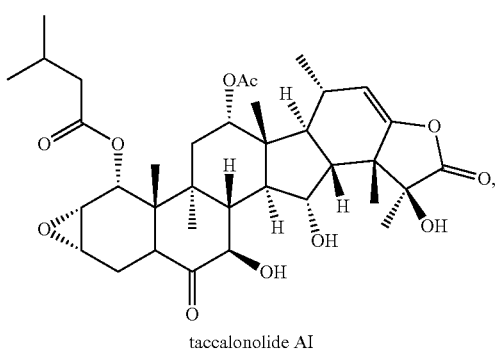

taccalonolide AI

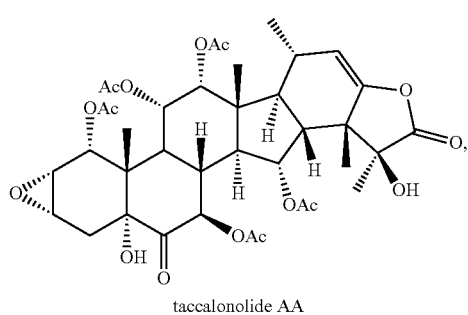

taccalonolide AA

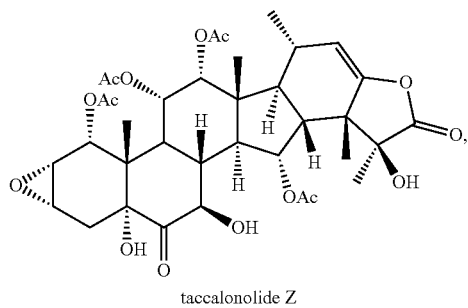

taccalonolide Z

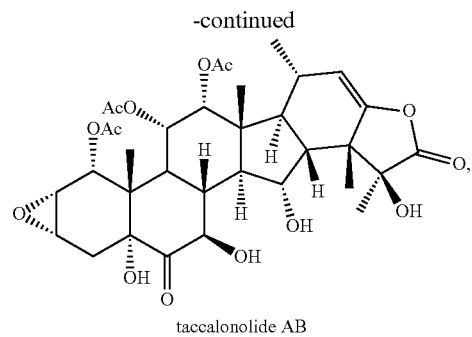

taccalonolide AB

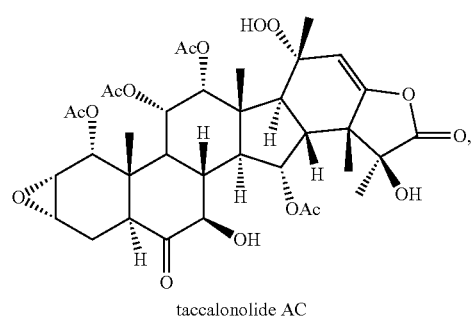

taccalonolide AC

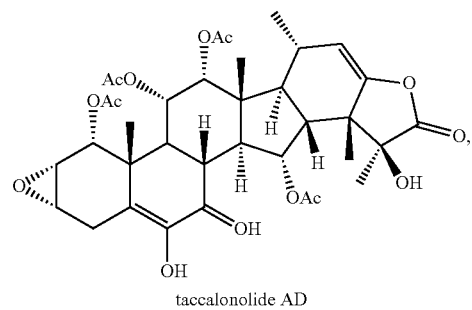

taccalonolide AD

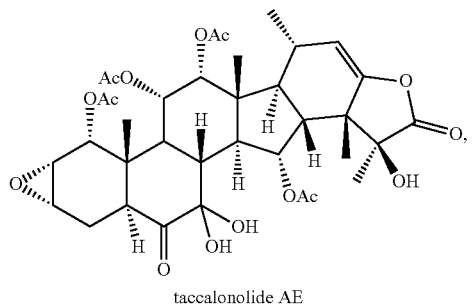
taccalonolide AE
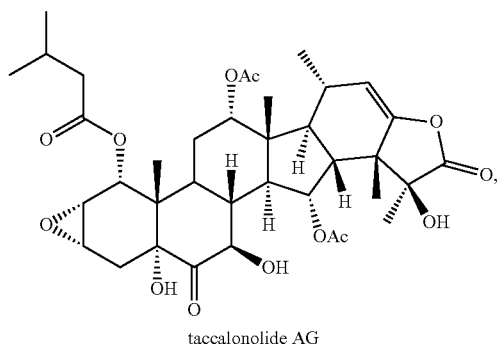
taccalonolide AG
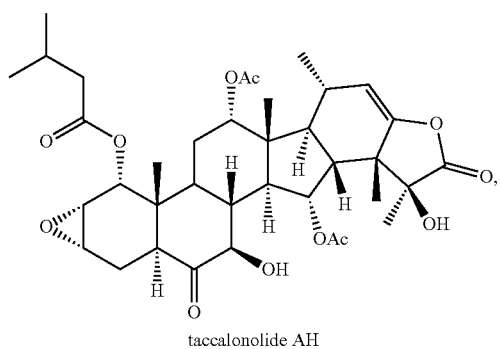
taccalonolide AH
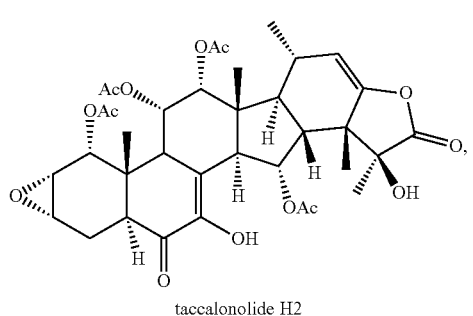
taccalonolide H2
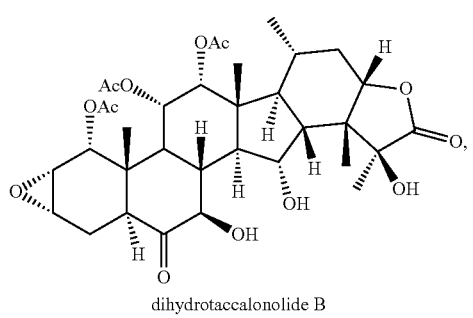
dihydrotaccalonolide B
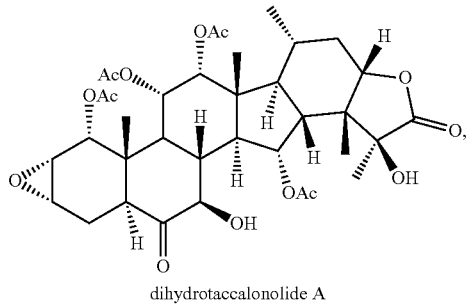
dihydrotaccalonolide A
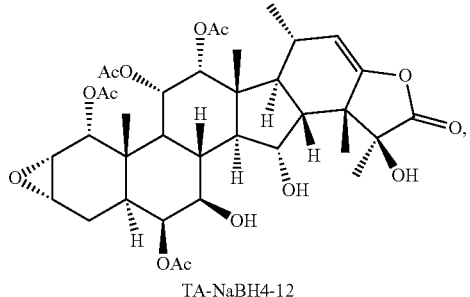
TA-NaBH4-12
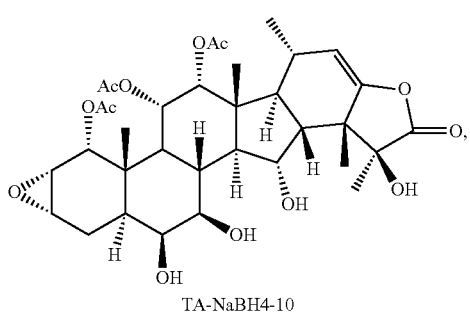
TA-NaBH4-10
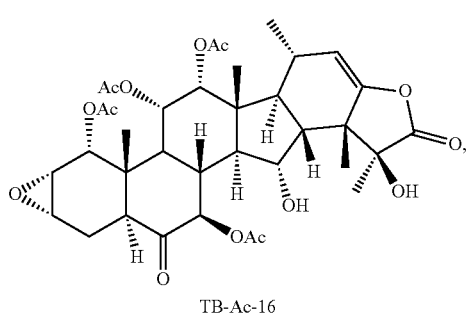
TB-Ac-16
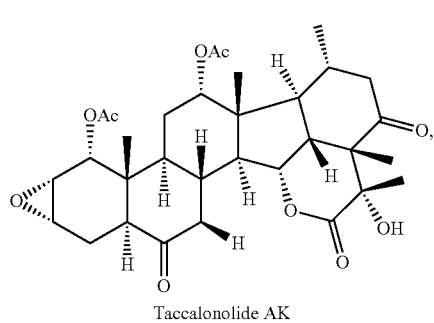
Taccalonolide AK -continued

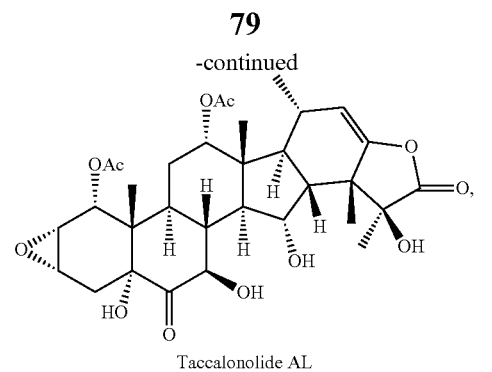

Taccalonolide AL

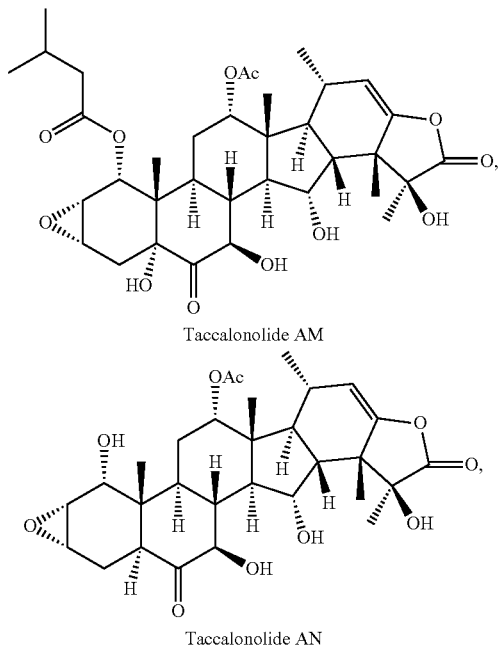

Taccalonolide AM

Taccalonolide AN

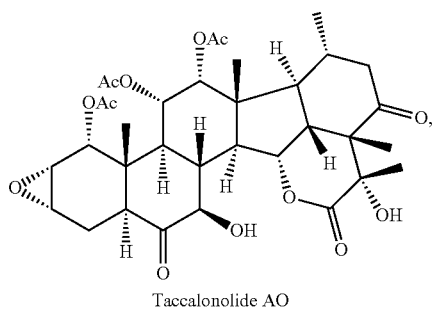

Taccalonolide AO

-continued

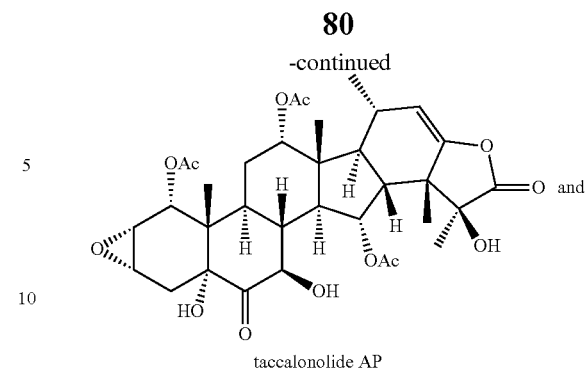

taccalonolide AP and

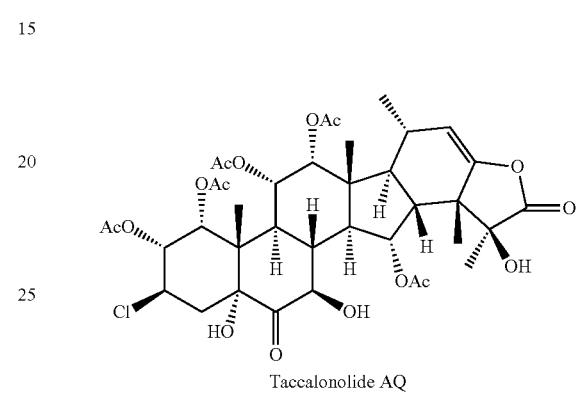

Taccalonolide AQ or a pharmaceutically acceptable salt thereof.

15. A method of treating a hyperproliferative disorder in a patient, wherein said hyperproliferative disorder is selected from the group consisting of breast cancer, ovarian cancer, lung cancer, cervical cancer and prostate cancer, the method comprising administering to a patient in need thereof an effective amount of a compound of claim 1.

16. A method of treating a hyperproliferative disorder in a patient, wherein said hyperproliferative disorder is selected from the group consisting of breast cancer, ovarian cancer, lung cancer, cervical cancer and prostate cancer, the method comprising administering to a patient in need thereof an effective amount of a composition of claim 13.

17. A compound according to claim 1 for the treatment of a hyperproliferative disorder in a patient, wherein said hyperproliferative disorder is selected from the group consisting of breast cancer, ovarian cancer, lung cancer, cervical cancer and prostate cancer.

* * * * *